United States Patent [19]

Schwing

[11] 4,348,220

[45] Sep. 7, 1982

[54] HERBICIDAL SULFONAMIDES

[75] Inventor: Gregory W. Schwing, Lincoln University, Pa.

[73] Assignee: E. I. Du Pont de Nemours and Company, Wilmington, Del.

[21] Appl. No.: 264,661

[22] Filed: May 27, 1981

Related U.S. Application Data

[63] Continuation-in-part of Ser. No. 168,350, Jul. 11, 1980, abandoned.

[51] Int. Cl.$^3$ .................... A01N 43/54; A01N 43/66; C07D 230/42
[52] U.S. Cl. ........................................ 71/92; 71/93; 544/211; 544/253; 544/278; 544/321; 544/332; 560/12
[58] Field of Search ................... 71/92, 93; 544/211, 544/253, 278, 321, 332

[56] References Cited

U.S. PATENT DOCUMENTS

| | | | |
|---|---|---|---|
| 4,127,405 | 11/1978 | Levitt | 544/211 |
| 4,214,890 | 7/1980 | Levitt | 71/93 |
| 4,231,784 | 11/1980 | Levitt | 71/93 |
| 4,257,802 | 3/1981 | Levitt | 544/211 |

*Primary Examiner*—Paul M. Coughlan, Jr.

[57] ABSTRACT

This invention relates to a novel class of N-(heterocyclicaminocarbonyl)-o-alkoxymethylbenzene sulfonamide herbicides.

43 Claims, No Drawings

HERBICIDAL SULFONAMIDES

RELATED APPLICATIONS

This application is a continuation-in-part of my co-pending application U.S. Ser. No. 168,350, filed July 11, 1980, now abandoned.

BACKGROUND OF THE INVENTION

This invention relates to novel compounds of Formula I, to compositions containing them and to their method of use as general and selective pre- and post-emergence herbicides. The invention also includes novel intermediates useful in preparing the compounds of Formula I.

Netherlands Pat. No. 121,788, published Sept. 15, 1966, teaches the preparation of compounds of Formula (i), and their use as general or selective herbicides:

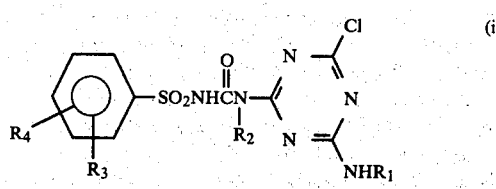

wherein $R_1$ and $R_2$ may independently be alkyl of 1-4 carbon atoms; and $R_3$ and $R_4$ may independently be hydrogen, chlorine or alkyl of 1-4 carbon atoms.

Compounds of Formula (ii), and their use as antidiabetic agents, are reported in J. Drug. Res. 6, 123 (1974):

wherein R is pyridyl.

In U.S. Pat. No. 4,127,405, compounds are disclosed of the general formula:

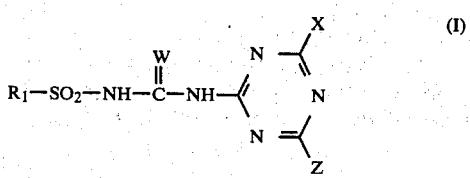

wherein $R_1$ is

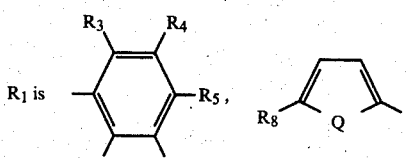

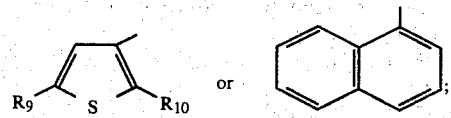

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S$— or $CH_3OCH_2$—; and Z is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In particular, the patent discloses orthosubstituted compounds wherein the substitution is $C_1$-$C_4$ alkyl.

The presence of undesired vegetation causes substantial damage to useful crops, especially agricultural products that satisfy man's basic food needs, such as soybeans, corn, wheat and the like. The current population explosion and concomitant world food shortage demand improvements in the efficiency of producing these crops. Preventing or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. However, the need exists for still more effective herbicides that destroy or retard weeds without causing significant damage to useful crops.

SUMMARY OF THE INVENTION

This invention relates to novel compounds of Formula I and their agriculturally suitable salts, suitable agricultural compositions containing them, and their method of use as general and selective pre-emergence and post-emergence herbicides and as plant growth regulants.

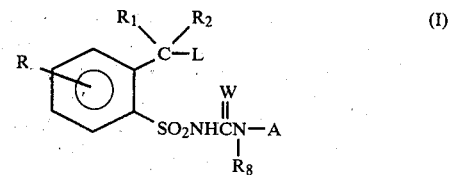

wherein

L is $S(O)_nR_7$ or $OR_9$;

R is H, F, Cl, Br, $NO_2$, $CF_3$, $C_1$-$C_3$ alkyl or $C_1$-$C_3$ alkoxy;

$R_1$ is H or $C_1-C_4$ alkyl;
$R_2$ is H or $CH_3$;
$R_7$ is $C_1-C_4$ alkyl;
$R_8$ is H, $CH_3$ or $OCH_3$;
$R_9$ is $C_1-C_6$ alkyl, $C_3-C_4$ alkenyl, $CH_2CF_3$, $CF_2CF_2H$ or $C_5-C_6$ cycloalkyl;
n is 0, 1 or 2;
A is

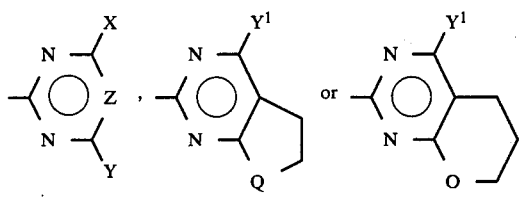

W is O or S;
X is H, Cl, Br, $CH_3$, $CH_2CH_3$, $C_1-C_3$ alkoxy, $CF_3$, $SCH_3$ or $CH_2OCH_3$;
Y is $CH_3$ or $OCH_3$;
Z is N, CH, CCl, CBr, CCN, $CCH_3$, $CCH_2CH_3$, $CCH_2CH_2Cl$ or $CCH_2CH=CH_2$;
$Y^1$ is H, $CH_3$, $OCH_3$ or $OCH_2CH_3$; and
Q is O or $CH_2$;
and their agriculturally suitable salts; provided that when n is 1, then W is O; and when W is S, then $R_8$ is H.

PREFERRED COMPOUNDS

Preferred in increasing order for their higher activity and/or more favorable ease of synthesis are: (1) Compounds of the generic scope wherein Z is N, CH, CCl, CBr or $CCH_3$; W is O; and $R_8$ is H or $CH_3$; (2) Compounds of Preferred (1) wherein Z is N or CH, X is $CH_3$ or $OCH_3$, provided that when n is 1 or 2, then Z is CH; (3) Compounds of Preferred (2) wherein A is

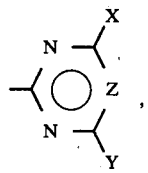

and R, $R_1$, $R_2$ and $R_8$ are H;
(4) Compounds of Preferred (3) wherein $R_9$ is $C_1-C_4$ alkyl; and
(5) Compounds of Preferred (4) wherein $R_7$ and $R_9$ are $CH_3$.

Specifically Preferred for highest activity and/or most favorable ease of synthesis are:
N-[(4,6-Dimethylpyrimidin-2-yl)aminocarbonyl]-2-methoxymethyl)benzenesulfonamide;
N-[(4-Methoxy-6-methylpyrimidin-2-yl)aminocarbonyl]-2-(methoxymethyl)benzenesulfonamide;
N-[(4,6-Dimethoxypyrimidin-2-yl)aminocarbonyl]-2-(methoxymethyl)benzenesulfonamide;
N-[(4,6-Dimethyl-1,3,5-triazin-2-yl)aminocarbonyl]-2-(methoxymethyl)benzenesulfonamide;
N-[(4-Methoxy-6-methyl-1,3,5-triazin-2-yl)aminocarbonyl]-2-(methoxymethyl)benzenesulfonamide;
N-[(4,6-Dimethoxy-1,3,5-triazin-2-yl)aminocarbonyl]-2-(methoxymethyl)benzenesulfonamide;
N-[(4,6-dimethylpyrimidin-2-yl)aminocarbonyl]-2-(methylthiomethyl)benzenesulfonamide;
N-[(4-Methoxy-6-methylpyrimidin-2-yl)aminocarbonyl]-2-(methylthiomethyl)benzenesulfonamide;
N-[(4,6-Dimethoxypyrimidin-2-yl)aminocarbonyl]-2-(methylthiomethyl)benzenesulfonamide;
N-[(4,6-Dimethyl-1,3,5-triazin-2-yl)aminocarbonyl]-2-(methylthiomethyl)benzenesulfonamide;
N-[(4-Methoxy-6-methyl-1,3,5-triazin-2-yl)aminocarbonyl]-2-(methylthiomethyl)benzenesulfonamide;
N-[(4,6-Dimethoxy-1,3,5-triazin-2-yl)aminocarbonyl]-2-(methylthiomethyl)benzenesulfonamide;
N-[(4,6-Dimethylpyrimidin-2-yl)aminocarbonyl]-2-(methylsulfinylmethyl)benzenesulfonamide;
N-[(4-Methoxy-6-methylpyrimidin-2-yl)aminocarbonyl]-2-(methylsulfonylmethyl)benzenesulfonamide;
N-[(4-Methoxy-6-methylpyrimidin-2-yl)aminocarbonyl]-2-(methylsulfinylmethyl)benzenesulfonamide.
N-[(4,6-Dimethoxypyrimidin-2-yl)aminocarbonyl]-2-(methylsulfonylmethyl)benzenesulfonamide;
N-[(4,6-Dimethoxypyrimidin-2-yl)aminocarbonyl]-2-(methylsulfinylmethyl)benzenesulfonamide; and
N-[(4,6-Dimethylpyrimidin-2-yl)aminocarbonyl]-2-(methylsulfonylmethyl)benzenesulfonamide.
N-[(4,6-dimethoxypyrimidin-2-yl)aminocarbonyl]-2-(butoxymethyl)benzenesulfonamide;
N-[(4,6-dimethoxypyrimidin-2-yl)aminocarbonyl]-2-(ethoxymethyl)benezenesulfonamide;
N-[(4,6-dimethoxypyrimidin-2-yl)aminocarbonyl]-2-(1-methylpropyloxymethyl)benezenesulfonamide.

This invention also relates to novel compounds of Formula II which are useful intermediates for the preparation of herbicidal compounds of Formula I.

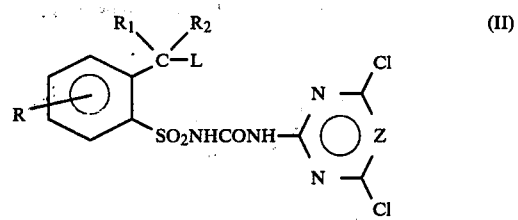

wherein
L, R, $R_1$, $R_2$, $R_7$ and $R_9$ are as previously defined;
n is 0 or 2; and
Z is CH or N.

This invention also relates to novel compounds of Formula III which are useful intermediates for the preparation of the compounds of Formula I.

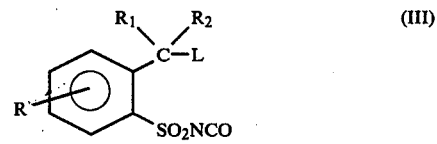

wherein
L, R, $R_1$, $R_2$, $R_7$ and $R_9$ are as previously defined, and;
n is 0 or 2.

Preferred are compounds of Formula III wherein R is H, Cl, Br or $OCH_3$;
$R_1$ is H or $CH_3$;
$R_2$ is H;
$R_7$ is $C_1-C_2$ alkyl; and
$R_9$ is $C_1-C_2$ alkyl.

Specifically preferred are 2-(methoxymethyl) benzenesulfonylisocyanate and 2-(methylthiomethyl)benzenesulfonylisocyanate.

DETAILED DESCRIPTION OF THE INVENTION

As shown in Equation 1, the compounds of Formula I can be prepared by reacting an appropriate 2-aminoheterocycle of Formula IV with an appropriately substituted sulfonyl isocyanate of Formula III; R, $R_1$, L, $R_2$, $R_8$ and A being as previously defined; and wherein n is 0 or 2.

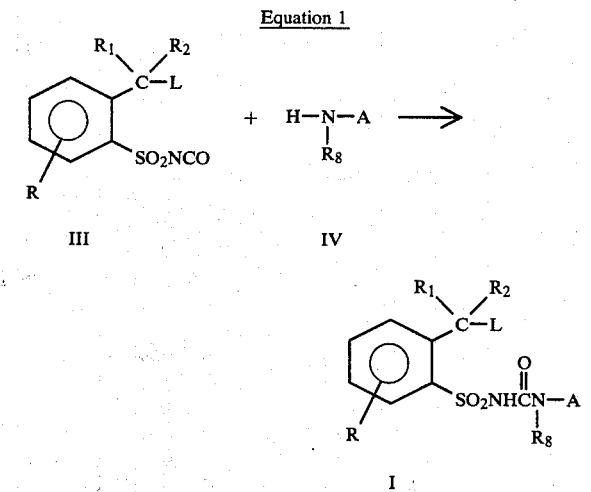

Equation 1

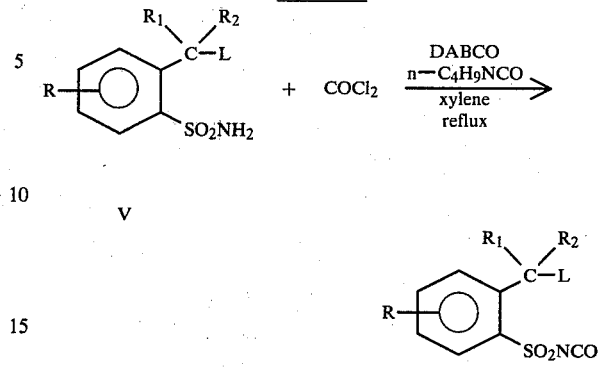

Equation 2

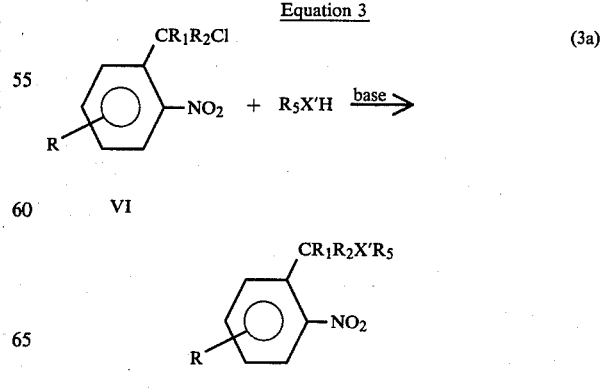

Equation 3

A mixture of the appropriate benzenesulfonamide V, an alkyl isocyanate and a catalytic amount of 1,4-diaza[2,2,2]bicyclooctane (DABCO) in xylene or other inert solvent of sufficiently high boiling point (e.g. $>135°$) is heated to approximately 135°. Phosgene is added to the mixture until an excess is present as indicated by a drop in the boiling point. (The mixture is heated further to drive off the excess phosgene). After the mixture is cooled and filtered to remove a small amount of insoluble by-products, the solvent and alkyl isocyanate are distilled in-vacuo leaving a residue which is the crude sulfonyl isocyanate III.

The preparation of these sulfonamides from sulfonyl chlorides with either ammonium hydroxide or anhydrous ammonia is widely reported in the literature, e.g. Crossley et al., *J. Am. Chem. Soc.*, 60, 2223 (1938), and P. A. Rossy et al., *J. Org. Chem.* 45, 617 (1980).

Benzenesulfonyl chlorides are best prepared by diazotization of the appropriate aniline with sodium nitrite in concentrated hydrochloric acid, followed by reaction of the diazonium salt with sulfur dioxide and cupric chloride in acetic acid according to the teaching of R. A. Abramovitch, *J. Org. Chem.* 43, 1218 (1978).

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of the aminoheterocycle. Since isocyanates usually are liquids, their addition is more easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether or pentane and filtration.

The intermediate sulfonyl isocyanate of Formula III can be prepared by reacting corresponding sulfonamides with phosgene in the presence of an alkyl isocyanate such as butyl or cyclohexyl isocyanate at reflux in a solvent such as chlorobenzene, according to the procedure of H. Ulrich and A. A. Y. Sayigh, *Newer Methods of Preparative Organic Chemistry*, Vol. VI, p. 223–241, Academic Press, New York and London, W. Foerst, Ed. In cases where information of the desired sulfonyl isocyanate is difficult by the above procedure, the performed sulfonylurea from the reaction of butyl isocyanate with the appropriate sulfonamide is treated with phosgene according to the above reference.

Alternatively, the process of Ulrich and Sayigh can be improved by the addition of a tertiary base to the reaction mixture as shown by Equation 2.

Anilines are obtained by reduction of the appropriate nitrobenzenes with iron powder in acetic acid as reported by D. C. Owsley and J. J. Bloomfield, Synthesis, 118 (1977).

The o-alkoxymethyl- or o-alkylthioymethylnitrobenzenes VII are in turn prepared via "Williamson Synthesis", according to Equations 3a or 3b.

-continued
Equation 3

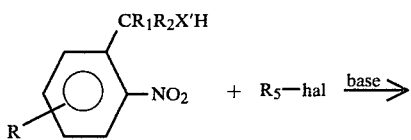
(3b)

VIII

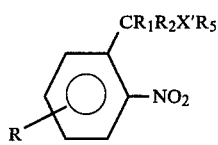

VII

X' = O or S, R$_5$ = R$_7$ or R$_8$.

"Williamson Synthesis" has been widely used for the preparation of ethers as reviewed by W. Theilheimer, Syn. Methods of Org. Chem., Vol. VII, p. 112.

Procedure 3a is most useful when R$_5$X' is a alkylthio or a primary alkoxy group, and R$_1$ and R$_2$ are both H. The reaction is carried out by mixing o-nitrobenzyl chloride and sodium methoxide or sodium alkylmercaptide (for preparation see Org. Syn., Coll. Vol. II, 345) in methanol under reflux or at room temperature, respectively.

Procedure 3a is, however, not applicable in cases where R$_5$X' is a branched alkoxy whose corresponding alkoxide anion is a stronger base than it is a nucleophile, and/or either R$_1$ or R$_2$ or both are alkyl groups. In the presence of a strong base and/or an α-alkyl substituent on o-nitrobenzyl chloride the base-catalyzed elimination rather than the desired SN$_2$ displacement occurs, giving rise to 2,2'-dinitrostilbene or other o-nitroalkenylbenzenes. In order to avoid these undesired reactions, a more general procedure, 3b, an be employed. The appropriate benzyl alcohol is first treated with base, such as sodium hydride, in an inert organic solvent, typically tetrahydrofuran or glyme, followed by displacement on an alkyl halide, as described by C. A. Brown and D. Barton, Synthesis, 434 (1974), and B. A. Stoochnoff and N. L. Benoiton, Tet. Lett., 21 (1973).

Alternatively, o-alkoxymethyl or o-alkylthio methylbenzenesulfonyl chlorides, XI, can be obtained from an appropriately substituted α-hydroxy-o-toluenesulfonic acid-α-sultone, IX, via ring-opening reaction with an alkoxide or alkylmercaptide anion as depicted in Equation 4.

Equation 4

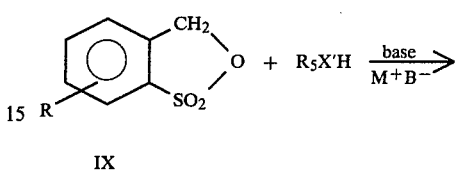
(4a)

IX

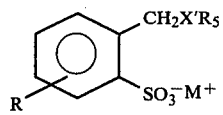

X

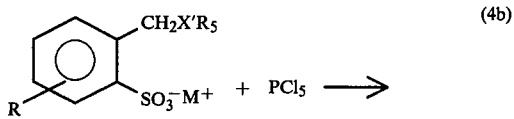
(4b)

X

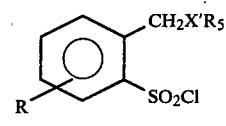

XI

Reaction 4a is closely related to the alkylation of acyloxides and acetamide with sultones as disclosed by J. H. Helberger et al., Ann., 565, 22 (1949). Conversion of the sulfonic acid salt to the sulfonyl chloride is then carried out according to the teaching of Org. Synthesis, Coll. Vol. IV, 846, 693.

Benzenesulfonamides of Formula XIII can also be derived from compound XII as illustrated in Equation 5.

Equation 5

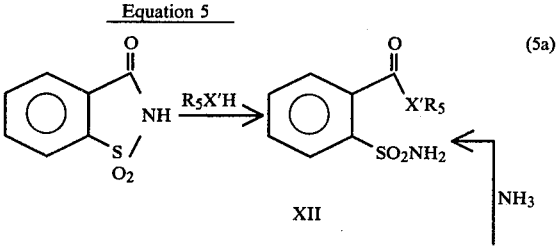
(5a)

XII

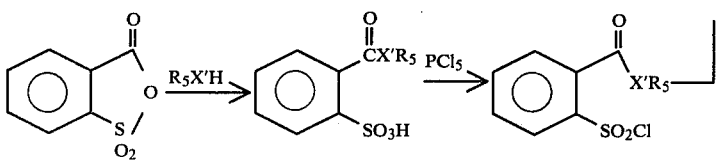

Equation 5

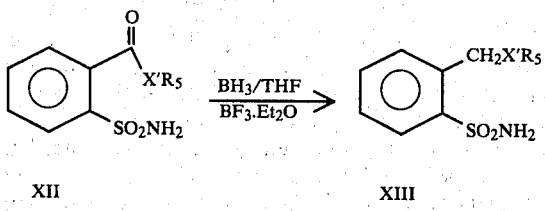

(5b)

Preparation of o-sulfamylbenzoic acid esters, XII, from saccharin or sulfobenzoic acid anhydride is well known in the art, e.g., B. Loev and M. Kormendy, *J. Org. Chem.* 27, 1703 (1962). The esters XII, can be readily reduced to the ethers XIII with diborane in a suitable organic solvent, e.g., tetrahydrofuran, in the presence of fifteen folds of boron trifluoride-etherate under reflux for 18 hours, as described by R. P. Graber and M. B. Meyers, *J. Org. Chem.* 26, 4773 (1961).

The o-alkylsulfinyl- and o-alkylsulfonylmethylbenzenesulfonylureas are made from their corresponding o-alkylthiomethylbenzenesulfonylureas by means of peroxide oxidation. Reaction of the sulfide-sulfonylurea with aqueous hydrogen peroxide in acetic acid at room temperature for half an hour affords exclusively the sulfoxidesulfonylurea. If the sulfide or sulfoxide is allowed to react for 72 hours under the same conditions, the sulfone is obtained. Oxidation for 20 hours often results in a mixture of both sulfoxide and sulfone, which can be readily separated by column chromatography and eluted with ethyl acetate. Sulfonylureas described above are generally stable under these reaction conditions. They will however, split into heterocyclicamine and o-alkylsulfonylbenzenesulfonamide if heated. A general procedure for peroxide oxidation of sulfides to sulfones can be found in the paper by A. M. Van Arendonk and E. C. Kliderer, *J. Am. Chem. Soc.*, 62, 3521 (1940).

The synthesis of heterocyclic amine derivatives has been reviewed in "The Chemistry of Heterocyclic Compounds", a series published by Interscience Publ., New York and London. 2-Aminopyrimidines are described by D. J. Brown in "The Pyrimidines", Vol. XVI of the above series.

2-Amino-1,3,5-triazines can be synthesized according to the methods described by E. M. Smolin and L. Rapaport in "s-Triazines and Derivatives", Vol. XIII of the same series.

The preparation of fused ring pyrimidine amines are disclosed in various publications, such as: Braken et al., *J. Am. Chem. Soc.*, 69, 3072 (1947); Nitten and Bharlacharya, *Quart. J. Ind. Chem. Soc.*, 4, 152 (1927), Schrage and Hitchings, *J. Org. Chem.*, 16, 1153 (1951); Svab et al., *Coll. Czech Commun.* 32, 1582 (1967); and unexamined European Patent 15683.

Many of the compounds of this invention can also be made by the method shown below.

The intermediates of Formula II, where R, $R_1$, $R_2$ and L are defined as above, Z is CH or N and n is 0, are novel and can conveniently be prepared by reacting a sulfonamide of Formula V with a 4,6-dichloroheterocyclic isocyanate of Formula XIV.

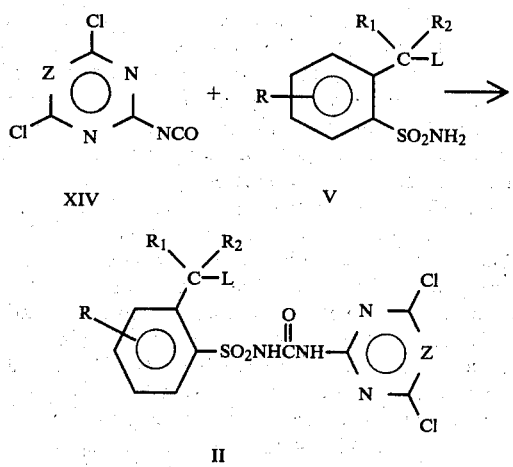

One or both of the halogen atoms on the heterocyclic ring of the compound of Formula II can be displaced by an alkoxide of 1-3 carbons to give compounds of Formula XV, where $R_6$ is $C_1$-$C_3$ alkyl and Y" is Cl or $OCH_3$.

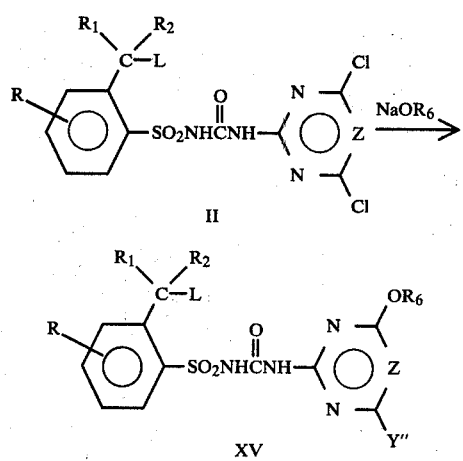

The process for the preparation of compounds of Formula XIV and XV is described in copending patent applications U.S. Ser. No. 193,190 and U.S. Ser. No. 192,681.

As shown in Equation 6, compounds of Formula I, in which W is sulfur and R, $R_1$, $R_2$ and A are as previously defined and $R_8$ is H are prepared by reaction of an appropriately substituted sulfonamide V with a heterocyclic isothiocyanate of Formula XVI.

Equation 6

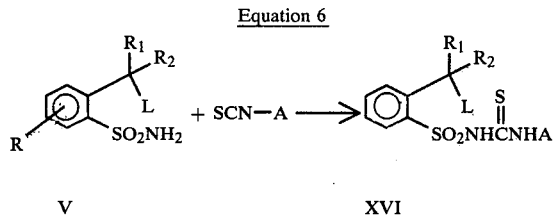

The reaction of Equation 6 is best carried out by dissolving or suspending the sulfonamide and isothiocyanate in a polar solvent such as acetone, acetonitrile, ethyl acetate or methylethylketone, adding an equivalent of a base such as potassium carbonate and stirring the mixture at ambient temperature up to the reflux temperature for one to twenty-four hours. In some cases, the product precipitates from the reaction mixture and can be removed by filtration. The product is stirred in dilute mineral acid, filtered and washed with cold water. If the product does not precipitate from the reaction mixture it can be isolated by evaporation of the solvent, trituration of the residue with dilute mineral acid and filtering off the insoluble product.

The heterocyclic isothiocyanates which are used in the procedure of Equation 6 are prepared, for example, according to the method of Japan Patent Application Pub: Kokai 51-143686, June 5, 1976, or that of W. Abraham and G. Barnikow, Tetrahedron 29, 691–7 (1973).

Compounds of Formula I wherein W is oxygen are also conveniently prepared by reacting the appropriately substituted sulfonamide V with the appropriate methyl pyrimidinyl carbamate or methyltriazinyl carbamate in the presence of an equimolar amount of trimethylaluminum according to the procedure of Equation 7.

Equation 7

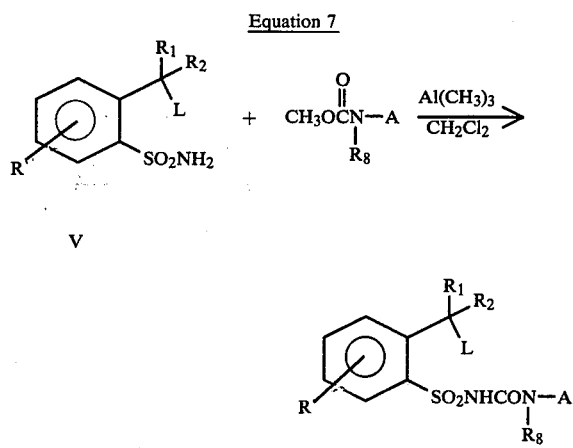

The reaction of Equation 7 is best carried out in methylene chloride at 25°0 to 40° for 24 to 96 hours under a nitrogen atmosphere. The product is isolated by the addition of an aqueous acetic acid solution followed by extraction of the product into methylene chloride or direct filtration of a product of low solubility. The product is purified by trituration with solvents such as n-butyl chloride or ether or subjected to column chromatography.

In the following examples, all temperatures are °C. unless otherwise specified, all melting points are not corrected and all parts are by weight.

EXAMPLE 1 o-Methylthiomethylnitrobenzene

To a stirred solution of 10.8 g (0.2 mol) of sodium methoxide in 70 ml of methanol at room temperature was added dropwise 12 ml (10.8 g, 0.22 mol) of methyl mercaptan through a gas addition funnel connected to a dry-ice condenser. The resulting mixture was stirred at room temperature for 1 hour and then added dropwise to a stirred solution of 30.0 g (0.175 mole) of o-nitrobenzyl chloride in 120 ml of methanol over 1 hour, while the temperature rose to 40° C. The reaction mixture was then diluted with 300 ml of water, and extracted 3 times with methylene chloride. The methylene chloride extracts were washed with dilute hydrochloric acid, dried, and concentrated to afford 38.6 g (96%) of yellow oil.

NMR (CDCl$_3$)δ: 1.97 (3H, s, CH$_3$); 3.97 (2H, s, CH$_2$); 7.3–8.1 (4H, m, 4 aromatic H's).

EXAMPLE 2 o-Methylthiomethylaniline

Iron powder (60 g, 1.0 g-atom) was added slowly through a solid addition funnel to a solution of 53.5 g (0.29 mol) of o-methylthiomethylnitrobenzene in 210 ml of glacial acetic acid and 600 ml of absolute ethanol under reflux over a period of 45 minutes. The mixture was then refluxed for 3 hours. The iron powder was filtered off and the filtrate was diluted with 800 ml of water. The aqueous mixture was extracted twice with 200 ml ethyl acetate and twice with 200 ml ether. The combined organic extracts were washed with water, dried and concentrated to yield 48 g (75% pure) of orange oil.

NMR (CDCl$_3$)δ: 1.90 (3H, s, CH$_3$); 3.60 (2H, s, CH$_2$); 5.72 (2H, bs, NH$_2$); and 6.5–7.3 (4H, m, 4 aromatic H's).

EXAMPLE 3 o-Methylthiomethylbenzenesulfonyl chloride

To a mixture containing 48 g (75% pure, 0.23 mol) of o-methylthiomethylaniline in 280 ml of acetic acid and 90 ml of concentrated hydrochloric acid at 0° was added a solution of 20 g (0.3 mol) of sodium nitrite in 50 ml of water. The resulting diazonium salt solution was then added through a dropping funnel to a mixture of 50 ml of sulfur dioxide and 12 g of cupric chloride in 140 ml of acetic acid and 140 ml of ether at 0° C. The mixture was allowed to stand at 0° C. overnight and then poured into 1 l of ice-water. Extraction with ether, washing, drying and evaporation of the solvent gave 26 g (50%) of red oil.

NMR (CDCl$_3$)δ: 2.46 (3H, s, CH$_3$); 4.67 (2H, s, CH$_2$); 7.2–8.0 (4H, m, 4 aromatic H's); plus one equivalent of o-methylthiomethylchlorobenzene; 2.07 (3H, s, CH$_3$); 4.18 (2H, s, CH$_2$); and 7.0–7.5 (aromatic H's).

The product was used for the next step without further purification.

EXAMPLE 4 o-Methylthiomethylbenzenesulfonamide

To a solution of 26 g (50% pure, 55 mmol) of o-methylthiomethylbenzenesulfonyl chloride in 250 ml of methylene chloride was added 4.5 ml of anhydrous ammonia at 0°–5° over 1 hour. Stirring was continued at 0°–5° C. for 2 hours. The solid precipitate was filtered off and the filtrate was evaporated to dryness to afford 24.8 g of orange residue. The crude product was triturated in ether, resulting in light pink crystals: m.p. 119°–124° C.

NMR (CDCl$_3$)δ: 2.05 (3H, s, CH$_3$); 4.18 (2H, s, CH$_2$); 6.72 (2H, bs, NH$_2$); 7.2–7.8 (3H, m, aromatic H's, m- & p-); and 8.0 (1H, dd, aromatic H, o-).

EXAMPLE 5 o-Methylthiomethylbenzenesulfonyl isocyanate

Phosgene (2.5 ml, 35 mmol) was added portionwise into a nitrogen-purged mixture containing 6.8 g (31 mmol) of o-methylthiomethylbenzenesulfonamide, 0.1 g of DABCO, and 3.8 g (38 mmol) of n-butyl isocyanate in 60 ml of dry xylene, while the temperature was maintained at 130°–135° C. between additions. Stirring was continued for 1 hour at 130°–135° C. The mixture was cooled to room temperature and the solid was filtered off under nitrogen. The filtrate was concentrated to yield 9.0 g (theo 7.6 g) of oil: IR cm$^{-1}$ 2240 (N=C=O), no NH at ca 3300. The oil was taken up in 90 ml of dry methylene chloride.

EXAMPLE 6

[N-(4,6-Dimethylpyrimidin-2-yl)aminocarbonyl]-2-methylthiomethylbenzenesulfonamide A solution of o-methylthiomethylbenzenesulfonyl isocyanate in dry methylene chloride (15 ml of the above solution from Example 5, 5 mmol) was added with a syringe into a nitrogen-purged flask containing 0.6 g (5 mmol) of 2-amino-4,6-dimethylpyrimidine and a trace of DABCO. The mixture was refluxed for 2½ hours. The solvent was removed in-vacuo to yield 1.8 g of white solid: m.p. 173°–183° C. The unreacted pyrimidine can be removed by washing with dilute hydrochloric acid.

NMR (DMSO-d$_6$): 1.90 (3H, s, SCH$_3$); 2.37 (6H, pyrimidine 4 & 6-CH$_3$'s); 4.08 (2H, s, CH$_2$); 7.03 (1H, s, pyrimidine 5-H); 7.64 (3H, m, benzene H's, m- & p-); 8.16 (1H, m, benzene, H, o-); 10.6 (1H, bs, SO$_2$NHCONH); and SO$_2$NHCONH not detectable.

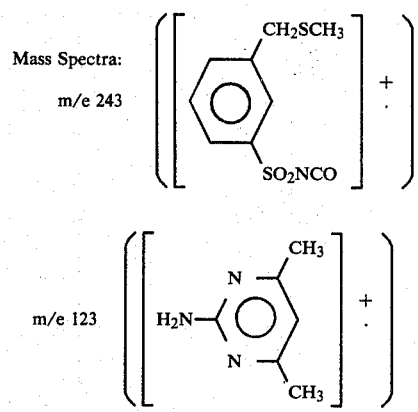

Mass Spectra: m/e 243 m/e 123

EXAMPLE 7

[N-(4,6-Dimethylpyrimidin-2-yl)aminocarbonyl]-2-methylsulfinylmethylbenzenesulfonamide One ml of 30% aqueous hydrogen peroxide was added to a suspension of 0.5 g (1.4 mmol) of [N-(4,6-dimethylpyrimidinyl)aminocarbonyl]-o-methylthiomethylbenzenesulfonamide in 15 ml of glacial acetic acid at room temperature. The mixture turned clear in 10 minutes and was stirred for a further 30 minutes. It was then diluted with water and extracted with methylene chloride. The organic extracts were washed, dried and concentrated to give 0.5 g (100%) of white solid: m.p. 176°184° C.

NMR (DMSO-d$_6$)δ: 2.40 (1H, s, pyrimidine 4- & 6-CH$_3$'s); 2.57 (3H, s, SCH$_3$);

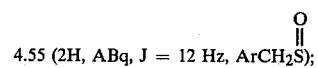

4.55 (2H, ABq, J = 12 Hz, ArCH$_2$S);

7.02 (1H, s, pyrimidine 5-H); 7.6 (3H, m, benzene m- & p- H's); 8.18 (1H, m, benzene, O-H); 10.5 (1H, bs, SO$_2$NHCONH); and SO$_2$NH not detectable.

EXAMPLE 8

[N-(4,6-Dimethylpyrimidin-2-yl)aminocarbonyl]-2-methylsulfonylmethylbenzenesulfonamide A mixture of 0.1 g (0.2 mmol) of [N-(4,6-dimethylpyrimidinyl)aminocarbonyl]-o-methylsulfinylmethylbenzenesulfonamide and 0.3 ml of 30% hydrogen peroxide in 5 ml of acetic acid was stirred at room temperature for 3 days. The resulting white solid precipitate was filtered to afford 30 mg of the desired product: m.p. 222°–225° C.

NMR (DMSO-d$_6$)δ: 2.42 (6H, s, pyrimidine 4- & 6-CH$_3$'s); 2.94 (3H, s, SCH$_3$); 5.10 (2H, s, CH$_2$); 7.00 (1H, s, pyrimidine 5-H); 7.7 (3H, m, benzene m- & p-H's); 8.1 (1H, m, benzene O-H); 10.5 (1H, bs, SO$_2$NH-CONH); and SO$_2$NH not detectable.

Using the proper reactants and the methods described above, the compounds in Tables I–VI can be prepared.

EXAMPLE 8a 2-(1-Methylethoxymethyl)benzenesulfonamide

To 4.9 g 2-(aminosulfonyl)benzoic acid, 1-methylethyl ester in 37 ml BF$_3$.Et$_2$O at a temperature 0°–10° was added over 45 min, 40 ml at 1 molar solution at BH$_3$ in THF. The mixture was refluxed overnight. The resulting cloudy yellow solution was concentrated on a rotary evaporator, acidified with 10% HCl, diluted with 300 ml H$_2$O and then extracted with three 100 ml portions of ether. The ether extracts were dried with magnesium sulfate and then concentrated to 4.1 g of wet solid. The product was further purufied to an oil by column chromatography on silica with methylene chloride.

NMR (CDCl$_3$)δ: 1.20 (6H, (CH$_3$)$_2$); 3.72 (1H, —CH); 4.88 (2H, CH$_2$); 7.2 (2H, MH$_2$); and 7.3–79 (4H, aromatic)

The product was converted to the corresponding sulfonylisocyanate by the procedure of Example 5. The resulting sulfonylisocyanate was used to prepare the corresponding sulfonylureas by the procedure of Example 6.

Using the proper reactants and the methods described above, the compounds of Tables I–VI can be prepared.

TABLE I

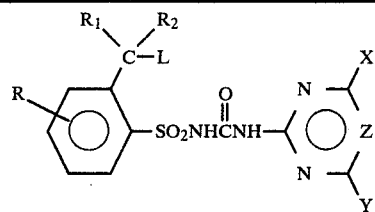

| L | R | R₁ | R₂ | X | Y | Z | m.p. (°C.) |
|---|---|---|---|---|---|---|---|
| OCH₃ | H | H | H | CH₃ | CH₃ | CH | 164–167° |
| OCH₃ | H | H | H | OCH₃ | CH₃ | CH | 163–166° |
| OCH₃ | H | H | H | OCH₃ | OCH₃ | CH | 171–176° |
| SCH₃ | H | H | H | CH₃ | CH₃ | CH | 173–183° |
| SCH₃ | H | H | H | OCH₃ | CH₃ | CH | 173–184° |
| SCH₃ | H | H | H | OCH₃ | OCH₃ | CH | 165–181° |
| O=SCH₃ | H | H | H | CH₃ | CH₃ | CH | 176–184° |
| O=SCH₃ | H | H | H | OCH₃ | CH₃ | CH | 142–150° |
| O=SCH₃ | H | H | H | OCH₃ | OCH₃ | CH | 178–184° |
| O=S(=O)CH₃ | H | H | H | CH₃ | CH₃ | CH | 222–225° |
| O=S(=O)CH₃ | H | H | H | OCH₃ | CH₃ | CH | 195–198° |
| O=S(=O)CH₃ | H | H | H | OCH₃ | OCH₃ | CH | 193–199° |
| OCH₃ | H | CH₃ | H | CH₃ | CH₃ | CH | |
| OCH₃ | H | CH₃ | H | OCH₃ | CH₃ | CH | |
| OCH₃ | H | CH₃ | H | OCH₃ | OCH₃ | CH | |
| SCH₃ | H | CH₃ | H | CH₃ | CH₃ | CH | |
| SCH₃ | H | CH₃ | H | OCH₃ | CH₃ | CH | |
| SCH₃ | H | CH₃ | H | OCH₃ | OCH₃ | CH | |
| O=SCH₃ | H | CH₃ | H | CH₃ | CH₃ | CH | |
| O=SCH₃ | H | CH₃ | H | OCH₃ | CH₃ | CH | |
| O=SCH₃ | H | CH₃ | H | OCH₃ | OCH₃ | CH | |
| O=S(=O)CH₃ | H | CH₃ | H | CH₃ | CH₃ | CH | |
| O=S(=O)CH₃ | H | CH₃ | H | OCH₃ | CH₃ | CH | |

TABLE I-continued

Structure: R-phenyl (with substituent $-C(R_1)(R_2)-L$ ortho) $-SO_2NHCNH-$ pyrimidine/triazine with X, Y, Z substituents.

| L | R | $R_1$ | $R_2$ | X | Y | Z | m.p. (°C.) |
|---|---|---|---|---|---|---|---|
| $\overset{O}{\underset{O}{\overset{\parallel}{\underset{\parallel}{S}}}}CH_3$ | H | $CH_3$ | H | $OCH_3$ | $OCH_3$ | CH | |
| $OCH_3$ | H | $CH_3$ | $CH_3$ | $CH_3$ | $CH_3$ | CH | |
| $OCH_3$ | H | $CH_3$ | $CH_3$ | $OCH_3$ | $CH_3$ | CH | |
| $OCH_3$ | H | $CH_3$ | $CH_3$ | $OCH_3$ | $OCH_3$ | CH | |
| $SCH_3$ | H | $CH_3$ | $CH_3$ | $CH_3$ | $CH_3$ | CH | |
| $SCH_3$ | H | $CH_3$ | $CH_3$ | $OCH_3$ | $CH_3$ | CH | |
| $SCH_3$ | H | $CH_3$ | $CH_3$ | $OCH_3$ | $OCH_3$ | CH | |
| $\overset{O}{\overset{\parallel}{S}}CH_3$ | H | $CH_3$ | $CH_3$ | $CH_3$ | $CH_3$ | CH | |
| $\overset{O}{\overset{\parallel}{S}}CH_3$ | H | $CH_3$ | $CH_3$ | $OCH_3$ | $CH_3$ | CH | |
| $\overset{O}{\overset{\parallel}{S}}CH_3$ | H | $CH_3$ | $CH_3$ | $OCH_3$ | $OCH_3$ | CH | |
| $\overset{O}{\underset{O}{\overset{\parallel}{\underset{\parallel}{S}}}}CH_3$ | H | $CH_3$ | $CH_3$ | $CH_3$ | $CH_3$ | CH | |
| $\overset{O}{\underset{O}{\overset{\parallel}{\underset{\parallel}{S}}}}CH_3$ | H | $CH_3$ | $CH_3$ | $OCH_3$ | $CH_3$ | CH | |
| $\overset{O}{\underset{O}{\overset{\parallel}{\underset{\parallel}{S}}}}CH_3$ | H | $CH_3$ | $CH_3$ | $OCH_3$ | $OCH_3$ | CH | |
| $OCH_2CH_3$ | H | H | H | $CH_3$ | $CH_3$ | CH | 133–140° |
| $OCH_2CH_3$ | H | H | H | $OCH_3$ | $CH_3$ | CH | 124–130° |
| $OCH_2CH_3$ | H | H | H | $OCH_3$ | $OCH_3$ | CH | 122–127° |
| $SCH_2CH_3$ | H | H | H | $CH_3$ | $CH_3$ | CH | |
| $SCH_2CH_3$ | H | H | H | $OCH_3$ | $CH_3$ | CH | |
| $SCH_2CH_3$ | H | H | H | $OCH_3$ | $OCH_3$ | CH | |
| $\overset{O}{\overset{\parallel}{S}}CH_2CH_3$ | H | H | H | $CH_3$ | $CH_3$ | CH | |
| $\overset{O}{\overset{\parallel}{S}}CH_2CH_3$ | H | H | H | $OCH_3$ | $CH_3$ | CH | |
| $\overset{O}{\overset{\parallel}{S}}CH_2CH_3$ | H | H | H | $OCH_3$ | $OCH_3$ | CH | |
| $\overset{O}{\underset{O}{\overset{\parallel}{\underset{\parallel}{S}}}}CH_2CH_3$ | H | H | H | $CH_3$ | $CH_3$ | CH | |

TABLE I-continued

Structure:

$R_1$, $R_2$ on C-L group attached to benzene ring with R substituent; benzene bears $-SO_2NHCNH-$ (with C=O) linked to pyrimidine/triazine ring with X, Y, Z substituents.

| L | R | $R_1$ | $R_2$ | X | Y | Z | m.p. (°C.) |
|---|---|---|---|---|---|---|---|
| $\overset{O}{\underset{O}{\overset{\|}{\underset{\|}{S}}}}CH_2CH_3$ | H | H | H | OCH$_3$ | CH$_3$ | CH | |
| $\overset{O}{\underset{O}{\overset{\|}{\underset{\|}{S}}}}CH_2CH_3$ | H | H | H | OCH$_3$ | OCH$_3$ | CH | |
| OCH(CH$_3$)$_2$ | H | H | H | CH$_3$ | CH$_3$ | CH | 165–171° |
| OCH(CH$_3$)$_2$ | H | H | H | OCH$_3$ | CH$_3$ | CH | 147–150° |
| OCH(CH$_3$)$_2$ | H | H | H | OCH$_3$ | OCH$_3$ | CH | 120–130° |
| SCH(CH$_3$)$_2$ | H | H | H | CH$_3$ | CH$_3$ | CH | |
| SCH(CH$_3$)$_2$ | H | H | H | OCH$_3$ | CH$_3$ | CH | |
| SCH(CH$_3$)$_2$ | H | H | H | OCH$_3$ | OCH$_3$ | CH | |
| $\overset{O}{\overset{\|}{S}}CH(CH_3)_2$ | H | H | H | CH$_3$ | CH$_3$ | CH | |
| $\overset{O}{\overset{\|}{S}}CH(CH_3)_2$ | H | H | H | OCH$_3$ | CH$_3$ | CH | |
| $\overset{O}{\overset{\|}{S}}CH(CH_3)_2$ | H | H | H | OCH$_3$ | OCH$_3$ | CH | |
| $\overset{O}{\underset{O}{\overset{\|}{\underset{\|}{S}}}}CH(CH_3)_2$ | H | H | H | CH$_3$ | CH$_3$ | CH | |
| $\overset{O}{\underset{O}{\overset{\|}{\underset{\|}{S}}}}CH(CH_3)_2$ | H | H | H | OCH$_3$ | CH$_3$ | CH | |
| $\overset{O}{\underset{O}{\overset{\|}{\underset{\|}{S}}}}CH(CH_3)_2$ | H | H | H | OCH$_3$ | OCH$_3$ | CH | |
| O(CH$_2$)$_3$CH$_3$ | H | H | H | CH$_3$ | CH$_3$ | CH | 136–142° |
| O(CH$_2$)$_3$CH$_3$ | H | H | H | OCH$_3$ | CH$_3$ | CH | 134–139° |
| O(CH$_2$)$_3$CH$_3$ | H | H | H | OCH$_3$ | OCH$_3$ | CH | 116–121° |
| OCH(CH$_3$)CH$_2$CH$_3$ | H | H | H | CH$_3$ | CH$_3$ | CH | 112–121° |
| OCH(CH$_3$)CH$_2$CH$_3$ | H | H | H | OCH$_3$ | CH$_3$ | CH | 125–128° |
| OCH(CH$_3$)CH$_2$CH$_3$ | H | H | H | OCH$_3$ | OCH$_3$ | CH | 114–116° |
| OCH$_3$ | H | H | H | CH$_3$ | CH$_3$ | N | 123–135° |
| OCH$_3$ | H | H | H | OCH$_3$ | CH$_3$ | N | 137–140° |
| OCH$_3$ | H | H | H | OCH$_3$ | OCH$_3$ | N | 138–143° |
| SCH$_3$ | H | H | H | CH$_3$ | CH$_3$ | N | 162–180° |
| SCH$_3$ | H | H | H | OCH$_3$ | CH$_3$ | N | 141–150° |
| SCH$_3$ | H | H | H | OCH$_3$ | OCH$_3$ | N | 113–133° |
| $\overset{O}{\overset{\|}{S}}CH_3$ | H | H | H | CH$_3$ | CH$_3$ | N | 169–172° |
| $\overset{O}{\overset{\|}{S}}CH_3$ | H | H | H | OCH$_3$ | CH$_3$ | N | 166–171° |
| $\overset{O}{\overset{\|}{S}}CH_3$ | H | H | H | OCH$_3$ | OCH$_3$ | N | 161–167° |

TABLE I-continued

| L | R | R₁ | R₂ | X | Y | Z | m.p. (°C.) |
|---|---|---|---|---|---|---|---|
| $\underset{O}{\overset{O}{\underset{\|}{\overset{\|}{S}}}}CH_3$ | H | H | H | CH₃ | CH₃ | N | 212–216° |
| $\underset{O}{\overset{O}{\underset{\|}{\overset{\|}{S}}}}CH_3$ | H | H | H | OCH₃ | CH₃ | N | 185–189° |
| $\underset{O}{\overset{O}{\underset{\|}{\overset{\|}{S}}}}CH_3$ | H | H | H | OCH₃ | OCH₃ | N | 189–195° |
| OCH₃ | H | CH₃ | H | CH₃ | CH₃ | N | |
| OCH₃ | H | CH₃ | H | OCH₃ | CH₃ | N | |
| OCH₃ | H | CH₃ | H | OCH₃ | OCH₃ | N | |
| SCH₃ | H | CH₃ | H | CH₃ | CH₃ | N | |
| SCH₃ | H | CH₃ | H | OCH₃ | CH₃ | N | |
| SCH₃ | H | CH₃ | H | OCH₃ | OCH₃ | N | |
| $\overset{O}{\overset{\|}{S}}CH_3$ | H | CH₃ | H | CH₃ | CH₃ | N | |
| $\overset{O}{\overset{\|}{S}}CH_3$ | H | CH₃ | H | OCH₃ | CH₃ | N | |
| $\overset{O}{\overset{\|}{S}}CH_3$ | H | CH₃ | H | OCH₃ | OCH₃ | N | |
| $\underset{O}{\overset{O}{\underset{\|}{\overset{\|}{S}}}}CH_3$ | H | CH₃ | H | CH₃ | CH₃ | N | |
| $\underset{O}{\overset{O}{\underset{\|}{\overset{\|}{S}}}}CH_3$ | H | CH₃ | H | OCH₃ | CH₃ | N | |
| $\underset{O}{\overset{O}{\underset{\|}{\overset{\|}{S}}}}CH_3$ | H | CH₃ | H | OCH₃ | OCH₃ | N | |
| OCH₃ | H | CH₃ | CH₃ | CH₃ | CH₃ | N | |
| OCH₃ | H | CH₃ | CH₃ | OCH₃ | CH₃ | N | |
| OCH₃ | H | CH₃ | CH₃ | OCH₃ | OCH₃ | N | |
| SCH₃ | H | CH₃ | CH₃ | CH₃ | CH₃ | N | |
| SCH₃ | H | CH₃ | CH₃ | OCH₃ | CH₃ | N | |
| SCH₃ | H | CH₃ | CH₃ | OCH₃ | OCH₃ | N | |
| $\overset{O}{\overset{\|}{S}}CH_3$ | H | CH₃ | CH₃ | CH₃ | CH₃ | N | |

TABLE I-continued $$\text{structure with } R, R_1, R_2, C-L, SO_2NHC(O)NH-\text{pyrimidine}(X, Y, Z)$$

| L | R | R₁ | R₂ | X | Y | Z | m.p. (°C.) |
|---|---|----|----|---|---|---|------------|
| $\underset{SCH_3}{\overset{O}{\|}}$ | H | CH₃ | CH₃ | OCH₃ | CH₃ | N | |
| $\underset{SCH_3}{\overset{O}{\|}}$ | H | CH₃ | CH₃ | OCH₃ | OCH₃ | N | |
| $\underset{\underset{O}{\|}}{\overset{O}{\underset{SCH_3}{\|}}}$ | H | CH₃ | CH₃ | CH₃ | CH₃ | N | |
| $\underset{\underset{O}{\|}}{\overset{O}{\underset{SCH_3}{\|}}}$ | H | CH₃ | CH₃ | OCH₃ | CH₃ | N | |
| $\underset{\underset{O}{\|}}{\overset{O}{\underset{SCH_3}{\|}}}$ | H | CH₃ | CH₃ | OCH₃ | OCH₃ | N | |
| OCH₂CH₃ | H | H | H | CH₃ | CH₃ | N | |
| OCH₂CH₃ | H | H | H | OCH₃ | CH₃ | N | 118–124° |
| OCH₂CH₃ | H | H | H | OCH₃ | OCH₃ | N | 131–140° |
| SCH₂CH₃ | H | H | H | CH₃ | CH₃ | N | |
| SCH₂CH₃ | H | H | H | OCH₃ | CH₃ | N | |
| SCH₂CH₃ | H | H | H | OCH₃ | OCH₃ | N | |
| $\underset{SCH_2CH_3}{\overset{O}{\|}}$ | H | H | H | CH₃ | CH₃ | N | |
| $\underset{SCH_2CH_3}{\overset{O}{\|}}$ | H | H | H | OCH₃ | CH₃ | N | |
| $\underset{SCH_2CH_3}{\overset{O}{\|}}$ | H | H | H | OCH₃ | OCH₃ | N | |
| $\underset{\underset{O}{\|}}{\overset{O}{\underset{SCH_2CH_3}{\|}}}$ | H | H | H | CH₃ | CH₃ | N | |
| $\underset{\underset{O}{\|}}{\overset{O}{\underset{SCH_2CH_3}{\|}}}$ | H | H | H | OCH₃ | CH₃ | N | |
| $\underset{\underset{O}{\|}}{\overset{O}{\underset{SCH_2CH_3}{\|}}}$ | H | H | H | OCH₃ | OCH₃ | N | |
| OCH(CH₃)₂ | H | H | H | CH₃ | CH₃ | N | 134–137° |
| OCH(CH₃)₂ | H | H | H | OCH₃ | CH₃ | N | |
| OCH(CH₃)₂ | H | H | H | OCH₃ | OCH₃ | N | |
| SCH(CH₃)₂ | H | H | H | CH₃ | CH₃ | N | |
| SCH(CH₃)₂ | H | H | H | OCH₃ | CH₃ | N | |
| SCH(CH₃)₂ | H | H | H | OCH₃ | OCH₃ | N | |
| $\underset{SCH(CH_3)_2}{\overset{O}{\|}}$ | H | H | H | CH₃ | CH₃ | N | |

TABLE I-continued

| L | R | R₁ | R₂ | X | Y | Z | m.p. (°C.) |
|---|---|---|---|---|---|---|---|
| $\overset{O}{\underset{}{\|}}$<br>SCH(CH₃)₂ | H | H | H | OCH₃ | CH₃ | N | |
| $\overset{O}{\underset{}{\|}}$<br>SCH(CH₃)₂ | H | H | H | OCH₃ | OCH₃ | N | |
| $\overset{O}{\underset{O}{\|\|}}$<br>SCH(CH₃)₂ | H | H | H | CH₃ | CH₃ | N | |
| $\overset{O}{\underset{O}{\|\|}}$<br>SCH(CH₃)₂ | H | H | H | OCH₃ | CH₃ | N | |
| $\overset{O}{\underset{O}{\|\|}}$<br>SCH(CH₃)₂ | H | H | H | OCH₃ | OCH₃ | N | |
| O(CH₂)₃CH₃ | H | H | H | CH₃ | CH₃ | N | 98–105° |
| O(CH₂)₃CH₃ | H | H | H | OCH₃ | CH₃ | N | 84–98° |
| O(CH₂)₃CH₃ | H | H | H | OCH₃ | OCH₃ | N | 125–128° |
| OCHCH₂CH₃<br>\|<br>CH₃ | H | H | H | CH₃ | CH₃ | N | 105–110° |
| OCHCH₂CH₃<br>\|<br>CH₃ | H | H | H | OCH₃ | OCH₃ | N | 112–121° |
| OCH₃ | H | H | H | Cl | CH₃ | N | |
| OC₂H₅ | H | CH₃ | H | CH₃ | CH₃ | N | |
| $\overset{O}{\underset{}{\|}}$<br>SCH₃ | H | CH₃CH₂ | H | CH₃CH₂ | OCH₃ | CH | |
| OCH₂CH₂CH₃ | H | CH₃CH₂CH₂ | H | OCH₂CH₃ | CH₃ | N | |
| $\overset{O}{\underset{O}{\|\|}}$<br>SCH₂CH₃ | H | (CH₃)₂CH | H | OCH₂CH₂CH₃ | CH₃ | CH | |
| OCH(CH₃)₂ | H | CH(CH₂)₃ | H | CF₃ | CH₃ | N | |
| OCH(CH₃)CH₂CH₃ | H | CH₃CH—CH₂—<br>\|<br>CH₃ | H | Cl | OCH₃ | CH | |
| SCH₂CH₂CH₃ | H | CH₃<br>\|<br>CH₃—C—<br>\|<br>CH₃ | H | OCH₃ | OCH₃ | N | |
| SCH(CH₃)CH₂CH₃ | H | \|<br>CH₃—CHCH₂CH₃ | H | OCH₂CH₃ | OCH₃ | CH | |
| OC(CH₃)₃ | F | H | H | SCH₃ | CH₃ | N | |
| OCH₂CF₃ | 3-Cl | H | H | CH₃ | OCH₃ | CH | |

TABLE I-continued

| L | R | R₁ | R₂ | X | Y | Z | m.p. (°C.) |
|---|---|----|----|---|---|---|-----------|
| OCF$_2$CF$_2$H | 5-Br | H | H | CF$_3$ | OCH$_3$ | N | |
| OCH$_2$CH=CH$_2$ | 3-NO$_2$ | H | H | OCH$_2$CH$_3$ | CH$_3$ | CH | |
| OCH$_2$C(CH$_3$)=CH$_2$ | 4-CF$_3$ | H | H | OCH$_2$CH$_2$CH$_3$ | OCH$_3$ | N | |
| $\overset{O}{\underset{\parallel}{S}}$CH$_2$CH$_2$CH$_3$ | 5-CH$_3$ | H | H | CH$_2$CH$_3$ | CH$_3$ | CH | |
| O—⟨cyclopentyl⟩ | H | H | H | CH$_3$ | CH$_3$ | CH | |
| O—⟨cyclohexyl⟩ | H | H | H | CH$_3$ | OCH$_3$ | N | |
| OCH$_3$ | H | H | H | Br | CH$_3$ | CH | |
| OCH$_3$ | H | H | H | CH$_2$OCH$_3$ | CH$_3$ | N | |
| $\overset{O}{\underset{\parallel}{\underset{O}{S}}}$CH(CH$_3$)$_2$ | 5-CH$_3$CH$_2$ | H | H | Br | CH$_3$ | N | |
| $\overset{O}{\underset{\parallel}{S}}$CH$_2$CH$_2$CH$_2$CH$_3$ | 6-CH$_3$CH$_2$CH$_2$ | H | H | CH$_3$ | CH$_3$ | CH | |
| $\overset{O}{\underset{\parallel}{\underset{O}{S}}}$C(CH$_3$)$_3$ | 3-(CH$_3$)$_2$CH | H | H | OCH$_3$ | CH$_3$ | N | |
| OCH$_2$CH$_2$CH$_2$CH$_3$ | 4-CH$_3$O | H | H | OCH$_3$ | OCH$_3$ | CH | |
| OCH$_2$CH$_2$CH=CH$_2$ | 5-CH$_3$CH$_2$O | H | H | OCH$_2$OCH$_3$ | OCH$_3$ | N | |
| OCH$_2$CH=CHCH$_3$ | 5-CH$_3$CH$_2$CH$_2$O | H | H | CH$_3$ | CH$_3$ | CH | |
| OCH$_2$CH(CH$_3$)$_2$ | 5-(CH$_3$)$_2$CHO | H | H | OCH$_3$ | CH$_3$ | N | |
| OCH$_3$ | H | H | H | OCH$_3$ | CH$_3$ | C—Cl | |
| SCH$_3$ | H | H | H | CH$_3$ | CH$_3$ | C—Br | |
| OC$_2$H$_5$ | H | H | H | OCH$_3$ | OCH$_3$ | C—CN | |
| OCH$_2$CH$_2$CH$_3$ | H | H | H | Cl | CH$_3$ | C—CH$_3$ | |
| $\overset{O}{\underset{\parallel}{S}}$CH$_3$ | H | H | H | Br | CH$_3$ | C—CH$_2$CH$_3$ | |
| $\overset{O}{\underset{\parallel}{\underset{O}{S}}}$CH$_3$ | H | H | H | OCH$_3$ | OCH$_3$ | C—CH$_2$CH$_2$Cl | |
| OCH(CH$_3$)$_2$ | H | H | H | OCH$_3$ | CH$_3$ | C—CH$_2$CH=CH$_2$ | |
| OC(CH$_3$)$_3$ | H | H | H | OCH$_3$ | OCH$_3$ | CH | |
| OCH$_2$CH$_2$CH$_2$CH$_3$ | H | H | H | OCH$_3$ | OCH$_3$ | N | |
| OCH$_2$CH(CH$_3$)$_2$ | H | H | H | OCH$_3$ | CH$_3$ | CH | |

TABLE Ia

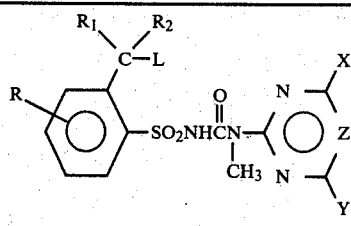

| L | R | R₁ | R₂ | X | Y | Z | m.p. (°C.) |
|---|---|---|---|---|---|---|---|
| OCH₃ | H | H | H | CH₃ | CH₃ | CH | |
| OCH₃ | H | H | H | OCH₃ | CH₃ | CH | |
| OCH₃ | H | H | H | OCH₃ | OCH₃ | CH | |
| SCH₃ | H | H | H | CH₃ | CH₃ | CH | |
| SCH₃ | H | H | H | OCH₃ | CH₃ | CH | |
| SCH₃ | H | H | H | OCH₃ | OCH₃ | CH | |
| O=S(CH₃) | H | H | H | CH₃ | CH₃ | CH | |
| O=S(CH₃) | H | H | H | OCH₃ | CH₃ | CH | |
| O=S(CH₃) | H | H | H | OCH₃ | OCH₃ | CH | |
| O=S(CH₃)=O | H | H | H | CH₃ | CH₃ | CH | |
| O=S(CH₃)=O | H | H | H | OCH₃ | CH₃ | CH | |
| O=S(CH₃)=O | H | H | H | OCH₃ | OCH₃ | CH | |
| OCH₃ | H | CH₃ | H | CH₃ | CH₃ | CH | |
| OCH₃ | H | CH₃ | H | OCH₃ | CH₃ | CH | |
| OCH₃ | H | CH₃ | H | OCH₃ | OCH₃ | CH | |
| SCH₃ | H | CH₃ | H | CH₃ | CH₃ | CH | |
| SCH₃ | H | CH₃ | H | OCH₃ | CH₃ | CH | |
| SCH₃ | H | CH₃ | H | OCH₃ | OCH₃ | CH | |
| O=S(CH₃) | H | CH₃ | H | CH₃ | CH₃ | CH | |
| O=S(CH₃) | H | CH₃ | H | OCH₃ | CH₃ | CH | |
| O=S(CH₃) | H | CH₃ | H | OCH₃ | OCH₃ | CH | |
| O=S(CH₃)=O | H | CH₃ | H | CH₃ | CH₃ | CH | |
| O=S(CH₃)=O | H | CH₃ | H | OCH₃ | CH₃ | CH | |
| O=S(CH₃)=O | H | CH₃ | H | OCH₃ | OCH₃ | CH | |
| OCH₃ | H | H | H | CH₃ | CH₃ | N | |
| OCH₃ | H | H | H | OCH₃ | CH₃ | N | |
| OCH₃ | H | H | H | OCH₃ | OCH₃ | N | |
| SCH₃ | H | H | H | CH₃ | CH₃ | N | |
| SCH₃ | H | H | H | OCH₃ | CH₃ | N | |
| SCH₃ | H | H | H | OCH₃ | OCH₃ | N | |
| O=S(CH₃) | H | H | H | CH₃ | CH₃ | N | |
| O=S(CH₃) | H | H | H | OCH₃ | CH₃ | N | |
| O=S(CH₃) | H | H | H | OCH₃ | OCH₃ | N | |
| O=S(CH₃)=O | H | H | H | CH₃ | CH₃ | N | |
| O=S(CH₃)=O | H | H | H | OCH₃ | CH₃ | N | |
| O=S(CH₃)=O | H | H | H | OCH₃ | OCH₃ | N | |
| OCH₃ | H | CH₃ | H | CH₃ | CH₃ | N | |
| OCH₃ | H | CH₃ | H | OCH₃ | CH₃ | N | |
| OCH₃ | H | CH₃ | H | OCH₃ | OCH₃ | N | |
| SCH₃ | H | CH₃ | H | CH₃ | CH₃ | N | |
| SCH₃ | H | CH₃ | H | OCH₃ | CH₃ | N | |
| SCH₃ | H | CH₃ | H | OCH₃ | OCH₃ | N | |
| O=S(CH₃) | H | CH₃ | H | CH₃ | CH₃ | N | |
| O=S(CH₃) | H | CH₃ | H | OCH₃ | CH₃ | N | |
| O=S(CH₃) | H | CH₃ | H | OCH₃ | OCH₃ | N | |
| O=S(CH₃)=O | H | CH₃ | H | CH₃ | CH₃ | N | |

TABLE Ia-continued

Structure: R-phenyl with C(R₁)(R₂)-L substituent, -SO₂NHC(O)N(CH₃)- linked to pyrimidine/triazine ring with X, Y, Z

| L | R | R₁ | R₂ | X | Y | Z | m.p. (°C.) |
|---|---|----|----|----|----|----|-----------|
| S(O)₂CH₃ | H | CH₃ | H | OCH₃ | CH₃ | N | |
| S(O)₂CH₃ | H | CH₃ | H | OCH₃ | OCH₃ | N | |

TABLE 1b

Structure: R-phenyl with C(R₁)(R₂)-L substituent, -SO₂NHC(O)N(OCH₃)- linked to ring with X, Y, Z

| L | R | R₁ | R₂ | X | Y | Z | m.p. (°C.) |
|---|---|----|----|----|----|----|-----------|
| OCH₃ | H | H | H | CH₃ | CH₃ | CH | |
| OCH₃ | H | H | H | OCH₃ | CH₃ | CH | |
| OCH₃ | H | H | H | OCH₃ | OCH₃ | CH | |
| SCH₃ | H | H | H | CH₃ | CH₃ | CH | |
| SCH₃ | H | H | H | OCH₃ | CH₃ | CH | |
| SCH₃ | H | H | H | OCH₃ | OCH₃ | CH | |
| S(O)CH₃ | H | H | H | CH₃ | CH₃ | CH | |
| S(O)CH₃ | H | H | H | OCH₃ | CH₃ | CH | |
| S(O)CH₃ | H | H | H | OCH₃ | OCH₃ | CH | |
| S(O)₂CH₃ | H | H | H | CH₃ | CH₃ | CH | |

TABLE 1b-continued

| L | R | R₁ | R₂ | X | Y | Z | m.p. (°C.) |
|---|---|----|----|----|----|----|-----------|
| S(O)₂CH₃ | H | H | H | OCH₃ | CH₃ | CH | |
| S(O)₂CH₃ | H | H | H | OCH₃ | OCH₃ | CH | |
| OCH₃ | H | CH₃ | H | CH₃ | CH₃ | CH | |
| OCH₃ | H | CH₃ | H | OCH₃ | CH₃ | CH | |
| OCH₃ | H | CH₃ | H | OCH₃ | OCH₃ | CH | |
| SCH₃ | H | CH₃ | H | CH₃ | CH₃ | CH | |
| SCH₃ | H | CH₃ | H | OCH₃ | CH₃ | CH | |
| SCH₃ | H | CH₃ | H | OCH₃ | OCH₃ | CH | |
| S(O)CH₃ | H | CH₃ | H | CH₃ | CH₃ | CH | |
| S(O)CH₃ | H | CH₃ | H | OCH₃ | CH₃ | CH | |
| S(O)CH₃ | H | CH₃ | H | OCH₃ | OCH₃ | CH | |
| S(O)₂CH₃ | H | CH₃ | H | CH₃ | CH₃ | CH | |
| S(O)₂CH₃ | H | CH₃ | H | OCH₃ | CH₃ | CH | |
| S(O)₂CH₃ | H | CH₃ | H | OCH₃ | OCH₃ | CH | |

TABLE II

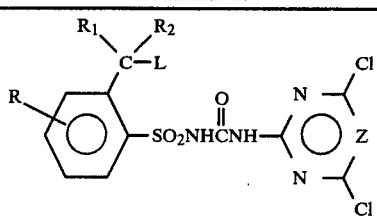

| L | R | R₁ | R₂ | Z | m.p. (°C.) |
|---|---|----|----|----|-----------|
| OCH₃ | H | H | H | CH | |
| OCH₃ | H | H | H | CH | |
| OCH₃ | H | H | H | CH | |
| SCH₃ | H | H | H | CH | |
| SCH₃ | H | H | H | CH | |

TABLE II-continued $$\text{R} \underset{}{\overset{R_1 \quad R_2}{\underset{|}{C-L}}} \text{—SO}_2\text{NHCNH—} \underset{}{\overset{O}{\|}} \text{pyrimidine/triazine with Cl, Z, Cl}$$

| L | R | $R_1$ | $R_2$ | Z | m.p. (°C.) |
|---|---|---|---|---|---|
| SCH₃ | H | H | H | CH | |
| S(O)₂CH₃ | H | H | H | CH | |
| S(O)₂CH₃ | H | H | H | CH | |
| S(O)₂CH₃ | H | H | H | CH | |
| OCH₃ | H | H | H | N | |
| OCH₃ | H | H | H | N | |
| OCH₃ | H | H | H | N | |
| SCH₃ | H | H | H | N | |
| SCH₃ | H | H | H | N | |
| SCH₃ | H | H | H | N | |
| S(O)₂CH₃ | H | H | H | N | |
| S(O)₂CH₃ | H | H | H | N | |
| S(O)₂CH₃ | H | H | H | N | |
| S(O)₂CH(CH₃)₂ | 3-CH₃CH₂ | H | H | N | |
| SCH₂CH₂CH₂CH₃ | 4-CH₃CH₂CH₂ | H | H | CH | |
| S(O)₂C(CH₃)₃ | 5-(CH₃)₂CH | H | H | N | |
| OCH₂CH₂CH₂CH₃ | 5-CH₃O | H | H | CH | |
| OCH₂CH₂CH=CH₂ | 5-CH₃CH₂O | H | H | N | |
| OCH₂CH=CHCH₂ | 4-CH₃CH₂CH₂O | H | H | CH | |
| OCH₂CH(CH₃)₂ | 6-(CH₃)₂CHO | H | H | N | |
| O-cyclopentyl | H | H | H | CH | |
| O-cyclohexyl | H | H | H | N | |
| OCH₃ | H | H | H | N | |
| SCH₃ | H | H | CH₃ | CH | |

TABLE II-continued

[Structure: R-substituted phenyl with C(R1)(R2)-L group ortho to SO2NHC(O)NH- linked to a pyrimidine/triazine bearing two CH2Cl groups and Z]

| L | R | R1 | R2 | Z | m.p. (°C.) |
|---|---|---|---|---|---|
| OC2H5 | H | CH3 | H | N | |
| SCH3 | H | CH3CH2 | H | CH | |
| OCH2CH2CH3 | H | CH3CH2CH2 | H | N | |
| $\underset{\underset{O}{\overset{O}{\|\|}}}{\overset{\|\|}{S}}$CH2CH3 | H | (CH3)2CH | H | CH | |
| OCH(CH3)2 | H | —CH(CH2)3 | H | N | |
| OCH(CH3)CH2CH3 | H | CH3CH—CH2— (with CH3 branch) | H | CH | |
| SCH2CH2CH3 | H | (CH3)3C—C(CH3)— | H | N | |
| SCH(CH3)CH2CH3 | H | CH3—CHCH2CH3 | H | CH | |
| OC(CH3)3 | 4-F | H | H | N | |
| OCH2CF3 | 5-Cl | H | H | CH | |
| OCF2CF2H | 5-Br | H | H | N | |
| OCH2CH=CH2 | 3-NO2 | H | H | CH | |
| OCH2C(CH3)=CH2 | 4-CF3 | H | H | N | |
| SCH2CH2CH3 | 6-CH3 | H | H | CH | |

TABLE III

[Structure: R-substituted phenyl with C(R1)(R2)-L group ortho to SO2NHC(O)NH- linked to a fused bicyclic pyrimidine with Y1 and Q substituents]

| L | R | R1 | R2 | Y1 | Q |
|---|---|---|---|---|---|
| OCH3 | H | H | H | CH3 | O |
| OCH3 | H | H | H | CH3O | O |
| SCH3 | H | H | H | CH3 | O |
| SCH3 | H | H | H | CH3O | O |
| $\overset{O}{\underset{}{\overset{\|\|}{S}}}$CH3 | H | H | H | CH3 | O |
| $\overset{O}{\underset{}{\overset{\|\|}{S}}}$CH3 | H | H | H | CH3O | O |
| $\underset{\underset{O}{\overset{O}{\|\|}}}{\overset{\|\|}{S}}$CH3 | H | H | H | CH3 | O |

TABLE III-continued

Structure:
R—(phenyl with ortho C(R₁)(R₂)—L substituent)—SO₂NHC(=O)NH—(pyrimidine with Y¹ and fused ring containing Q)

| L | R | R₁ | R₂ | Y¹ | Q |
|---|---|----|----|----|---|
| S(=O)(=O)CH₃ | H | H | H | CH₃O | O |
| OCH₃ | H | H | H | H | O |
| OCH₃ | H | H | H | CH₃ | CH₂ |
| OCH₃ | H | H | H | CH₃O | CH₂ |
| SCH₃ | H | H | H | H | O |
| SCH₃ | H | H | H | CH₃ | CH₂ |
| SCH₃ | H | H | H | CH₃O | CH₂ |
| OCH₃ | H | H | H | CH₃CH₂O | O |
| SCH₃ | H | CH₃ | CH₃ | CH₃ | O |
| OC₂H₅ | H | CH₃ | H | CH₃O | O |
| OCH₂CH₂CH₃ | H | CH₃CH₂CH₂ | H | H | O |
| S(=O)(=O)CH₂CH₃ | H | (CH₃)₂CH | H | CH₃ | CH₂ |
| OCH(CH₃)₂ | H | CH(CH₂)₃ | H | CH₃O | CH₂ |
| OCH(CH₃)CH₂CH₃ | H | CH₃CH—CH₂ (with CH₃) | H | CH₃ | O |
| SCH₂CH₂CH₃ | H | CH₃—C(CH₃)(CH₃) | H | CH₃O | O |
| OC(CH₃)₃ | 3-F | H | H | H | O |
| OCH₂CF₃ | 4-Cl | H | H | CH₃ | CH₂ |
| OCF₂CF₂H | 5-Br | H | H | CH₃O | CH₂ |
| OCH₂CH=CH₂ | 5-NO₂ | H | H | CH₃ | O |
| OCH₂C(CH₃)=CH₂ | 6-CF₃ | H | H | CH₃O | O |
| O—cyclopentyl | H | H | H | CH₃ | O |
| O—cyclohexyl | H | H | H | CH₃ | CH₂ |
| S(=O)(=O)CH(CH₃)₂ | 3-CH₃CH₂ | H | H | H | O |
| S(=O)(=O)CH₂CH₂CH₂CH₃ | 4-CH₃CH₂CH₂ | H | H | CH₃ | CH₂ |

TABLE III-continued

| L | R | R₁ | R₂ | Y¹ | Q |
|---|---|---|---|---|---|
| $\underset{O}{\overset{O}{\underset{\|}{\overset{\|}{S}}}}C(CH_3)_3$ | 5-(CH₃)₂CH | H | H | CH₃O | CH₂ |
| OCH₂CH₂CH₂CH₃ | 5-CH₃O | H | H | CH₃ | O |
| OCH₂CH₂CH=CH₂ | 5-CH₃CH₂O | H | H | CH₃O | O |
| OCH₂CH(CH₃)₂ | 5-(CH₃)₂CHO | H | H | H | O |

TABLE IV

| L | R | R₁ | R₂ | Y¹ | Q |
|---|---|---|---|---|---|
| OCH₃ | H | H | H | CH₃ | O |
| OCH₃ | H | H | H | CH₃O | O |
| SCH₃ | H | H | H | CH₃ | O |
| SCH₃ | H | H | H | CH₃O | O |
| $\overset{O}{\underset{\|}{S}}CH_3$ | H | H | H | CH₃ | O |
| $\overset{O}{\underset{\|}{S}}CH_3$ | H | H | H | CH₃O | O |
| $\underset{O}{\overset{O}{\underset{\|}{\overset{\|}{S}}}}CH_3$ | H | H | H | CH₃ | O |
| $\underset{O}{\overset{O}{\underset{\|}{\overset{\|}{S}}}}CH_3$ | H | H | H | CH₃O | O |
| OCH₃ | H | H | H | H | O |
| OCH₃ | H | H | H | CH₃ | CH₂ |
| OCH₃ | H | H | H | CH₃O | CH₂ |
| SCH₃ | H | H | H | H | O |
| SCH₃ | H | H | H | CH₃ | CH₂ |
| SCH₃ | H | H | H | CH₃O | CH₂ |
| OCH₃ | H | H | H | CH₃CH₂O | CH₂ |
| SCH₃ | H | CH₃ | CH₃ | CH₃ | O |
| OC₂H₅ | H | CH₃ | H | CH₃O | O |
| OCH₂CH₂CH₃ | H | CH₃CH₂CH₂ | H | H | O |
| $\underset{O}{\overset{O}{\underset{\|}{\overset{\|}{S}}}}CH_2CH_3$ | H | (CH₃)₂CH | H | CH₃ | CH₂ |
| OCH(CH₃)₂ | H | CH(CH₂)₃ | H | CH₃O | CH₂ |

TABLE IV-continued

Structure: R-phenyl with C(R1)(R2)-L substituent, SO2NHC(O)NH-pyrimidine with Y1, fused ring with Q and O.

| L | R | R1 | R2 | Y1 | Q |
|---|---|----|----|----|----|
| OCH(CH3)CH2CH3 | H | CH3CH—CH2 (with CH3 branch) | H | CH3 | O |
| SCH2CH2CH3 | H | (CH3)3C— | H | CH3O | O |
| OC(CH3)3 | 3-F | H | H | H | O |
| OCH2CF3 | 4-Cl | H | H | CH3 | CH2 |
| OCF2CF2H | 5-Br | H | H | CH3O | CH2 |
| OCH2CH=CH2 | 5-NO2 | H | H | CH3 | O |
| OCH2C(CH3)=CH2 | 6-CF3 | H | H | CH3O | O |
| O-cyclopentyl | H | H | H | CH3 | O |
| O-cyclohexyl | H | H | H | CH3 | CH2 |
| S(O)2CH(CH3)2 | 3-CH3CH2 | | | H | O |
| S(O)2CH2CH2CH2CH3 | 4-CH3CH2CH2 | H | H | CH3 | CH2 |
| S(O)2C(CH3)3 | 5-(CH3)2CH | H | H | CH3O | CH2 |
| OCH2CH2CH2CH3 | 5-CH3O | H | H | CH3 | O |
| OCH2CH2CH=CH2 | 5-CH3CH2O | H | H | CH3O | O |
| OCH2CH(CH3)2 | 5-(CH3)2CHO | H | H | H | O |

TABLE V

Structure: R-phenyl with C(R1)(R2)-L and SO2NCO substituents.

| L | R | R1 | R2 |
|---|---|----|----|
| OCH3 | H | H | H |
| OCH3 | H | H | CH3 |
| OCH3 | H | CH3 | CH3 |
| SCH3 | H | H | H |
| SCH3 | H | H | CH3 |
| SCH3 | H | CH3 | CH3 |
| S(O)2CH3 | H | H | H |
| S(O)2CH3 | H | H | CH3 |
| S(O)2CH3 | H | CH3 | CH3 |
| OCH3 | H | C2H5 | H |
| OC2H5 | H | CH3 | H |
| SCH3 | H | CH3CH2 | H |
| OCH2CH2CH3 | H | CH3CH2CH2 | H |

TABLE V-continued

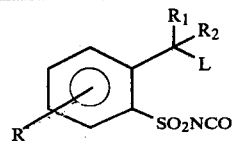

| L | R | R₁ | R₂ |
|---|---|---|---|
| $\overset{O}{\underset{O}{\overset{\|}{\underset{\|}{S}}}}CH_2CH_3$ | H | (CH₃)₂CH | H |
| OCH(CH₃)₂ | H | CH(CH₂)₃ | H |
| OCH(CH₃)CH₂CH₃ | H | CH₃CH—CH₂ <br>         \|<br>        CH₃ | H |
| SCH₂CH₂CH₃ | H | CH₃—C(CH₃)₂—CH₃ | H |
| SCH(CH₃)CH₂CH₃ | H | CH₃—CHCH₂CH₃ | H |
| OC(CH₃)₃ | 4-F | H | H |
| OCH₂CF₃ | 5-Cl | H | H |
| OCF₂CF₂H | 5-Br | H | H |
| OCH₂CH=CH₂ | 3-NO₂ | H | H |
| OCH₂C(CH₃)=CH₂ | 4-CF₃ | H | H |
| SCH₂CH₂CH₃ | 6-CH₃ | H | H |
| $\overset{O}{\underset{O}{\overset{\|}{\underset{\|}{S}}}}CH(CH_3)_2$ | 3-CH₃CH₂ | H | H |
| $\overset{O}{\underset{O}{\overset{\|}{\underset{\|}{S}}}}C(CH_3)_3$ | 5-(CH₃)₂CH | H | H |
| OCH₂CH₂CH₂CH₃ | 5-CH₃O | H | H |
| OCH₂CH₂CH=CH₂ | 5-CH₃CH₂O | H | H |
| OCH₂CH(CH₃)₂ | 5-(CH₃)₂CHO | H | H |
| O—cyclopentyl | H | H | H |
| O—cyclohexyl | H | H | H |

TABLE VI

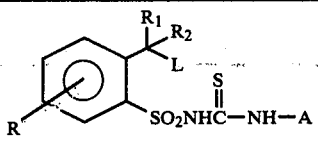

| L | R | R₁ | R₂ | A |
|---|---|---|---|---|
| OCH₃ | H | H | H |  2,5-dimethylpyrimidin-yl |

TABLE VI-continued

| L | R | R₁ | R₂ | A |
|---|---|---|---|---|
| OCH₃ | H | H | H | 4-methyl-6-methoxypyrimidin-yl |
| OCH₃ | H | H | H | 4,6-dimethoxypyrimidin-yl |
| OCH₃ | H | H | H | 2,6-dimethylpyrazin-yl |
| OCH₃ | H | H | H | 2-methyl-6-methoxypyrazin-yl |
| OCH₃ | H | H | H | 2,6-dimethoxypyrazin-yl |
| OCH₃ | H | H | H | 2,3-dihydrofuro[2,3-b]pyridinyl |
| OCH₃ | H | H | H | 5-methyl-6,7-dihydro-cyclopenta[b]pyridinyl |
| OCH₃ | H | H | H | 5-methyl-2,3-dihydrofuro[2,3-b]pyridinyl |

TABLE VI-continued
| | | | | |
|---|---|---|---|---|
| L | R | R₁ | R₂ | A |
| OCH₃ | H | H | H | 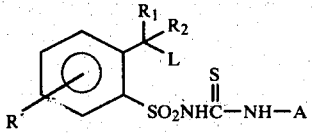 |
| OCH₃ | H | H | H | 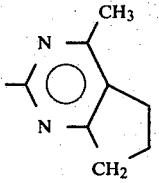 |
| OCH₃ | H | H | H | 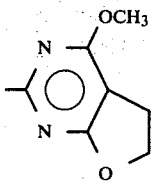 |
| OCH₃ | H | H | H | 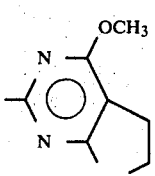 |
| OCH₃ | H | H | H | 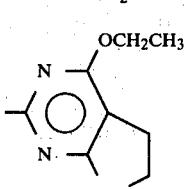 |
| OCH₃ | H | H | H | 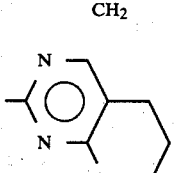 |
| OCH₃ | H | CH₃ | H | 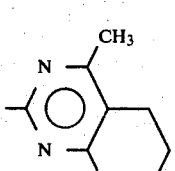 |
| OCH₃ | H | CH₃ | H | 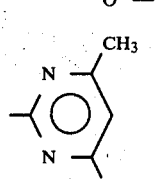 |
| OCH₃ | H | CH₃ | H | 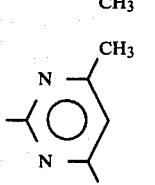 |
| OCH₃ | H | CH₃ | H |  |
| OCH₃ | H | CH₃ | H |  |
| OCH₃ | H | CH₃ | H | 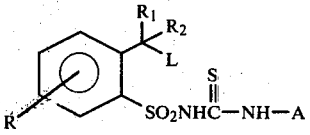 |
| OCH₃ | H | CH₃ | CH₃ | 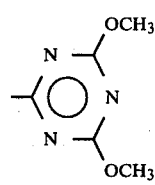 |
| OCH₃ | H | CH₃ | CH₃ | 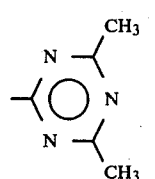 |
| SCH₃ | H | H | H | 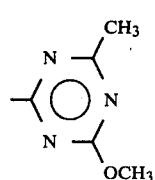 |
| SCH₃ | H | H | H | 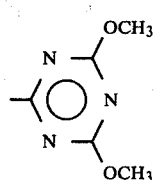 |

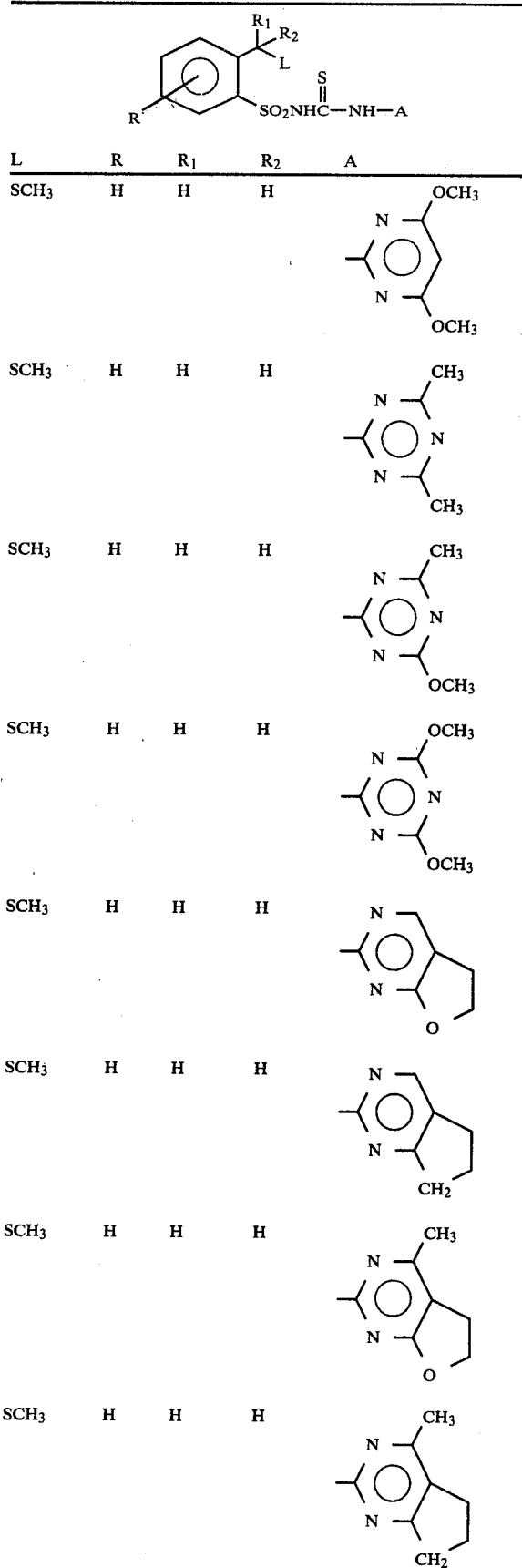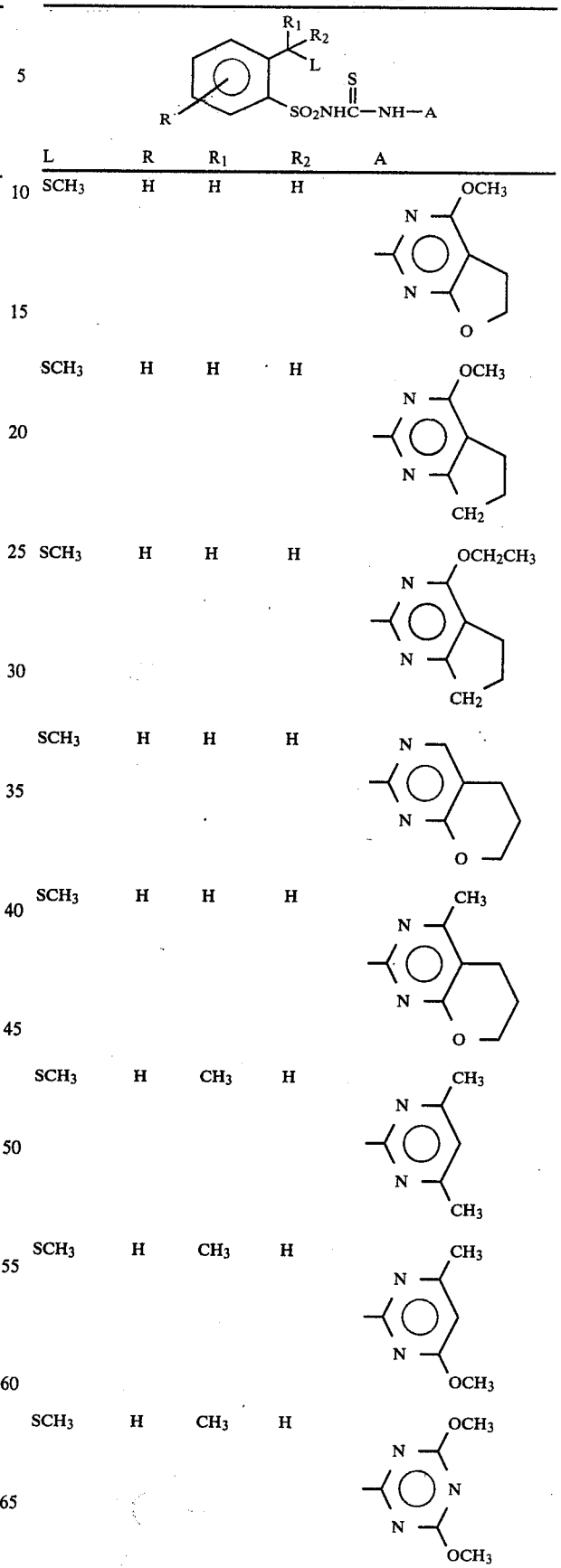

TABLE VI-continued

Structure: phenyl ring with R (on ring), R1, R2, L substituents, and SO2NHC(=S)NH—A group

| L | R | R1 | R2 | A |
|---|---|----|----|---|
| SCH3 | H | CH3 | H | 4,6-dimethylpyrimidin-2-yl |
| SCH3 | H | CH3 | H | 4-methyl-6-methoxypyrimidin-2-yl |
| SCH3 | H | CH3 | H | 4,6-dimethoxypyrimidin-2-yl |
| SCH3 | H | CH3 | CH3 | 4,6-dimethylpyrimidin-2-yl |
| SCH3 | H | CH3 | CH3 | 4-methyl-6-methoxypyrimidin-2-yl |
| S(O)2CH3 | H | H | H | 4,6-dimethylpyrimidin-2-yl |
| S(O)2CH3 | H | H | H | 4-methyl-6-methoxypyrimidin-2-yl |
| S(O)2CH3 | H | H | H | 4,6-dimethoxypyrimidin-2-yl |
| S(O)2CH3 | H | H | H | 4,6-dimethylpyrimidin-2-yl |
| S(O)2CH3 | H | H | H | 4-methyl-6-methoxypyrimidin-2-yl |
| S(O)2CH3 | H | H | H | 4,6-dimethoxypyrimidin-2-yl |
| S(O)2CH3 | H | H | H | furo-fused pyrimidinyl (methyl substituted) |
| S(O)2CH3 | H | H | H | cyclopenta-fused pyrimidinyl (methyl substituted) |
| S(O)2CH3 | H | H | H | 4-methyl-furo-fused pyrimidinyl |
| S(O)2CH3 | H | H | H | 4-methyl-cyclopenta-fused pyrimidinyl |
| S(O)2CH3 | H | H | H | 4-methoxy-furo-fused pyrimidinyl |

TABLE VI-continued

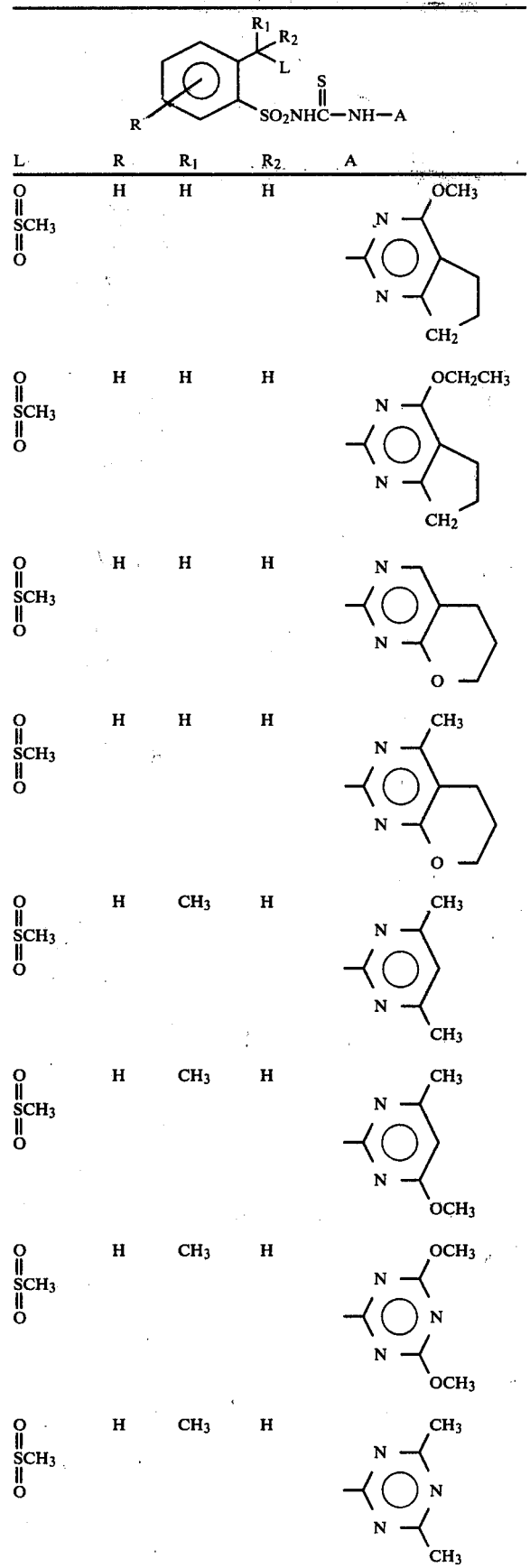

TABLE VI-continued

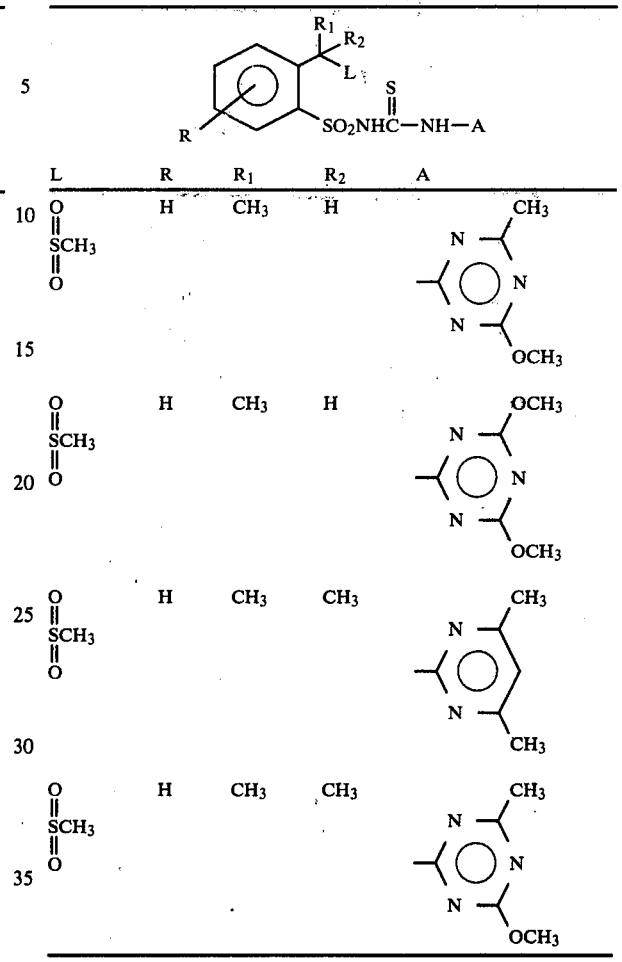

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VII

| | Active* Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |

TABLE VII-continued

|  | Active* Ingredient | Diluent(s) | Surfactant(s) |
|---|---|---|---|
| High Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood N.J., as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 1, line 62 and Examples 8, 12, 15, 39, 41, 52, 53, 58, 132, 138–140, 162–164, 166, 167 and 169–182.

H. Gysin and E. Knusli, U.S. Pat. No. 2,891,855, June 23, 1959, Col. 5, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 9

Wettable Powder

| | |
|---|---|
| N-[(4,6-dimethylpyrimidin-2-yl)aminocarbonyl]-2-(methoxymethyl)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 10

Wettable Powder

| | |
|---|---|
| N-[(4-methoxy-6-methylpyrimidin-2-yl-aminocarbonyl]-2-(methoxymethyl)-benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 11

Granule

| | |
|---|---|
| wettable powder of Example 10 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 12

Extruded Pellet

| | |
|---|---|
| N-[(4,6-dimethoxypyrimidin-2-yl)aminocarbonyl]-2-(methoxymethyl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

Oil Suspension

| | |
|---|---|
| N-[(4,6-dimethyl-1,3,5-triazin-2-yl)-aminocarbonyl]-2-(methoxymethyl)benzenesulfonamide | 25% |
| polyoxyethylene sorbital hexaoleate | 5% |

-continued

| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

Wettable Powder

| | |
|---|---|
| N-[4-methoxy-6-methyl-1,3,5-triazin-2-yl)aminocarbonyl]-2-(methoxymethyl)-benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 15

Low Strength Granule

| | |
|---|---|
| N-[4,6-dimethoxy-1,3,5-triazin-2-yl)-aminocarbonyl]-2-(methoxymethyl)-benzenesulfonamide | 1% |
| N,N-dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

Aqueous Suspension

| | |
|---|---|
| N-[4,6-dimethylpyrimidin-2-yl)aminocarbonyl]-2-(methylthiomethyl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| Water | 56.7% |

The ingredients are blended and ground together in a sand mill to produce particles essentially all under 5 microns in size.

EXAMPLE 17

Solution

| | |
|---|---|
| N-[(4-methoxy-6-methylpyrimidin-2-yl)-aminocarbonyl]-2-(methylthiomethyl)-benzenesulfonamide, sodium salt | 5% |

-continued

| water | 95% |

The salt is added directly to the water with stirring to produce the solution, which may then be packaged for use.

EXAMPLE 18

Low Strength Granule

| | |
|---|---|
| N-[(4,6-dimethoxypryimidin-2-yl)-aminocarbonyl]-2-(methylthiomethyl)benzenesulfonamide | 0.1% |
| attapulgite granules (U.S.S. 20–40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 19

Granule

| | |
|---|---|
| N-[(4,6-dimethyl-1,3,5-triazin-2-yl-aminocarbonyl]-2-(methylthiomethyl)-benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granule of the desired size range are made. The spraying is stopped, but fluidization is continued, optionally with heat, until the water constant is reduced to the desired level, generally less than 1%. The material is then discharged, screened to the desired size range, generally 14–100 mesh (1410–149 microns), and packaged for use.

EXAMPLE 20

High Strength Concentrate

| | |
|---|---|
| N-[(4-methoxy-6-methyl-1,3,5-triazin-2-yl)aminocarbonyl]-2-(methylthiomethyl)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 21

Wettable Powder

| | |
|---|---|
| N-[(4,6-dimethylpyrimidin-2-yl)amino-carbonyl]-2-(methylsulfonylmethyl)- | |

-continued

| | |
|---|---|
| benzenesulfonamide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 22

Wettable Powder

| | |
|---|---|
| N-[(4,6-dimethoxy-1,3,5-triazin-2-yl)-aminocarbonyl]-2-(methylthiomethyl)-benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 23

Oil Suspension

| | |
|---|---|
| N-[(4-methoxy-6-methylpyrimidin-2-yl)-aminocarbonyl]-2-(methylsulfonylmethyl)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 24

Dust

| | |
|---|---|
| N-[(4,6-dimethoxypyrimidin-2-yl)aminocarbonyl]-2-(methylthiomethyl)benzenesulfonamide | 10% |
| attapulgite | 10% |
| Pyrophyllite | 80% |

The active ingredient is blended with attapulgite and then passed through a hammer mill to produce particles substantially all below 200 microns. The ground concentrate is then blended with powdered pyrophyllite until homogeneous.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting compound rate, time and method of application, compounds of this invention may also be used to modify plant growth beneficially, or to selectively control weeds in cereal crops.

The precise amount of the compounds of Formula I to be used in any given situation will vary according to the particular end result desired, the amount of foliage present, the crop species involved, the types of weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.01 to 10 kg/ha. In general, the lower rates of application from within this range are suggested for use on lighter soils and/or those having a low organic matter content, for selective weed control or for plant growth regulation, whereas the higher rates will be selected for adverse conditions or where extended persistence in soil is desired.

The compounds of the invention may be used in combination with any other commercial herbicide examples of which are those of the triazine, triazole, uracil, urea, amide, diphenylether, carbamate bipyridylium types.

The activity of these compounds was discovered in greenhouse tests. The tests are described and the data resulting from them are shown below.

| | |
|---|---|
| 0 = | no effect |
| 10 = | maximum effect |
| C = | chlorosis or necrosis |
| D = | defoliation |
| E = | emergence inhibition |
| G = | growth retardation |
| H = | formative effects |
| U = | unusual pigmentation |
| X = | axillary stimulation |
| 6Y = | abscised buds or flowers |
| 6F = | delayed flowering. |
| S = | albinism |

TEST A

Seeds of crabgrass (Digitaria spp.), barnyardgrass (Echinochloa crusgalli), wild oats (Avena fatua), cassia (Cassia tora), morningglory (Ipomoea sp.), cocklebur (Xanthium spp.), sorghum, corn, soybean, rice, wheat and nutsedge tubers (Cyperus rotundus) were planted in a growth medium and treated pre-emergence with the chemicals dissolved in a non phytotoxic solvent solution of the compounds of Table A. At the same time, cotton having five leaves (including cotyledonary ones), bush beans with the third trifoliate leaf expanding, crabgrass, barnyardorass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed with a non-phytotoxic solvent solution of the compounds of Table A. Other containers of the above untreated weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment. The data in Table A shows that some compounds of this invention are very effective as herbicides and ofen cause little or no injury to cereal crops.

TABLE A

| Compound | kg/ha | BUSH-BEAN | COT-TON | MORN-ING-GLORY | COCK-LE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| ![structure with 2,6-diCH3 pyrimidine]  SO2NHCNH-, CH2OCH3 | 0.4 | 9C | 9C | 10C | 9C | 9C | 9C | 9C | 10C | 9C | 9C | 9C | 9C | 9C | 9C |
| ![2-CH3, 6-OCH3 pyrimidine] | 0.4 | 9C | 7C,9G | 10C | 10C | 9C | 9C | 9C | 10C | 9C | 9C | 9C | 9C | 9C | 10C |
| ![2,6-diOCH3 pyrimidine] | 0.4 | 9C | 9C | 10C | 10C | 9C | 9C | 9C | 9C | 9C | 9C | 9C | 9C | 9C | 9C |
| ![triazine 2-CH3, 6-CH3] | 0.4 | 9C | 9C | 10C | 10C | 9C | 9C | 6C,9G | 9C | 6C,9G | 9C | 9C | 9C | 9C | 10C |
| ![triazine 2-CH3, 6-OCH3] | 0.4 | 9C | 10C | 10C | 9C | 9C | 8C | 9C | 10C | 6C,9G | 9C | 10C | 9C | 10C | 10C |
| ![triazine 2-CH3, 6-OCH3 variant] | | | | | | | | | | 5C,9G | 10C | | | 10C | 10C |

TABLE A-continued

| Structure | | | | | | | | | | | | |
|---|---|---|---|---|---|---|---|---|---|---|---|---|
| ![structure with OCH3, OCH3 on pyrimidine, SO2NHCNH, CH2OCH3] | 0.4 | 9C | 10C | 10C | 9C | 9C | 2C,6G | 9C | 9C | 2C | 1C | 7C,9C | 9C | 1C,9H |
| ![structure with CH3, CH3 on pyrimidine, SO2NHCNH, CH2SCH3] | 0.4 | 3C,6Y, 7G | 3C,3H, 8G | 3C,8G | 3C | 5G | 1C,5G | 10C | 9C | 1C | 1C,5H | 1C,2G | 2C,8G | 2C,8G |
| ![structure with CH3, OCH3 on pyrimidine, SO2NHCNH, CH2SCH3] | 0.4 | 9C | 5C,9G | 5C,9G | 2C,6G | 2C,8G | 9C | 9C | 9C | 9C | 7U,9C | 6C,9G | 6C,9G | 3D,9G |
| ![structure with OCH3, OCH3 on pyrimidine, SO2NHCNH, CH2SCH3] | 0.4 | 9C | 10C | 10C | 6C,8G | | 10C | 9C | 9C | 5C,9G | 5D,9C | 9C | 5C,9G | 9C |
| ![structure with CH3, CH3 on pyrimidine, SO2NHCNH, CH2SCH3] | 0.4 | 3H,7G | 1H | 1H | 5C,9G | 0 | 0 | 0 | 0 | 0 | 0 | 1H | 0 | 0 |
| ![structure with CH3, OCH3 on pyrimidine, SO2NHCNH, CH2SCH3] | 0.4 | 6C,6Y, 9G | 3H,4C, 9G | 1C,2G | 4C,9G | 2C | 0 | 5H | 0 | 0 | 8H | 2C,7X, 8G | 2C,7G | 2C,8G |

TABLE A-continued

| Structure | | | | | | | | | | |
|---|---|---|---|---|---|---|---|---|---|---|
| Ar-SO2NHCNH-pyrimidine (CH2SCH3 substituent), OCH3/OCH3 | 0.4 | 2C,6Y, 9G | 2C,5H | 2C,7G | 2C,6G | 2C | 0 | 3H | 0 | 4C,9G | 2C,5X, 8G | 9C | 1C,6H |
| Ar-SO2NHCNH-pyrimidine (CH2SOCH3 substituent), CH3/CH3 | 0.4 | 4S,5G, 6F | 3C,5H | 3C,8H | 3C,5G | 1C | 2C,6G | 1C | 4C,8H | 4C,9H | 2C,7G | 2C,5G | 3H | 4C,9G | 1C,9G |
| Ar-SO2NHCNH-pyrimidine (CH2SO2CH3 substituent), CH3/OCH3 | 0.4 | 6C,6Y, 9G | 7C,9G | 10C | 6C,9G | 4C,7G | 2C,9G | 3C,7G | 4C,8H | 2C | 3U,9G | 2C,9G | 3C,8G |
| Ar-SO2NHCNH-pyrimidine (CH2SOCH3 substituent), OCH3/OCH3 | 0.4 | 6C,6Y, 9G | 6C,9G | 9C | 5C,9G | 6C,8G | 8G | 5C,9G | 9C | 4C,8G | 3C,6G | 5C,9G | 3C,9G | 5C,9G | 4U,9G |
| Ar-SO2NHCNH-pyrimidine (CH2SO2CH3 substituent), OCH3/OCH3 | 0.4 | 5C,6Y, 8G | 9C | 10C | 10C | 6C,9G | 6C,9G | 2C,7G | 9C | 0 | 3U,9H | 4C,9G | 3C,9G | 2U,9G |

TABLE A-continued
| Structure | | | | | | | | | | | | | | | |
|---|---|---|---|---|---|---|---|---|---|---|---|---|---|---|---|
| 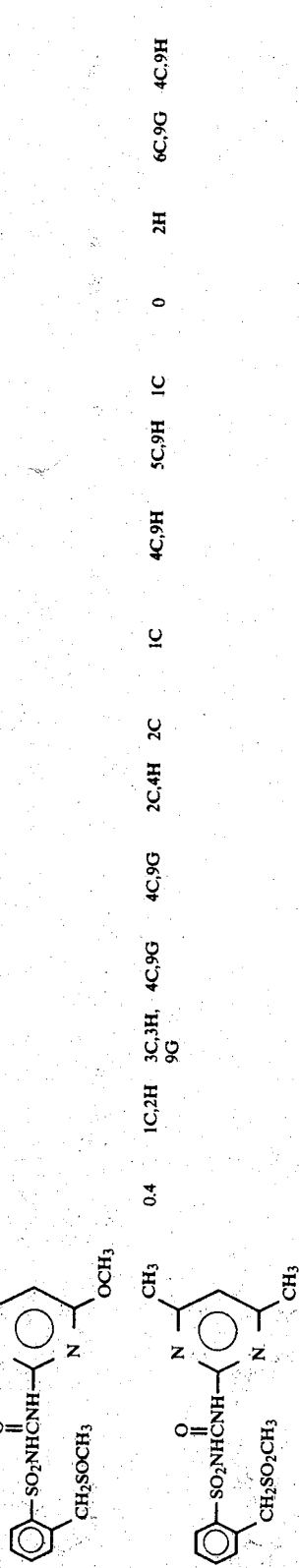 | 0.4 | 9C | 10C | 9C | 5C,9G | 2C,9G | 3C,9H | 9C | 3C,9H | 2C,4G | 10C | 6C,9G | 6C,9G | 9C |
| 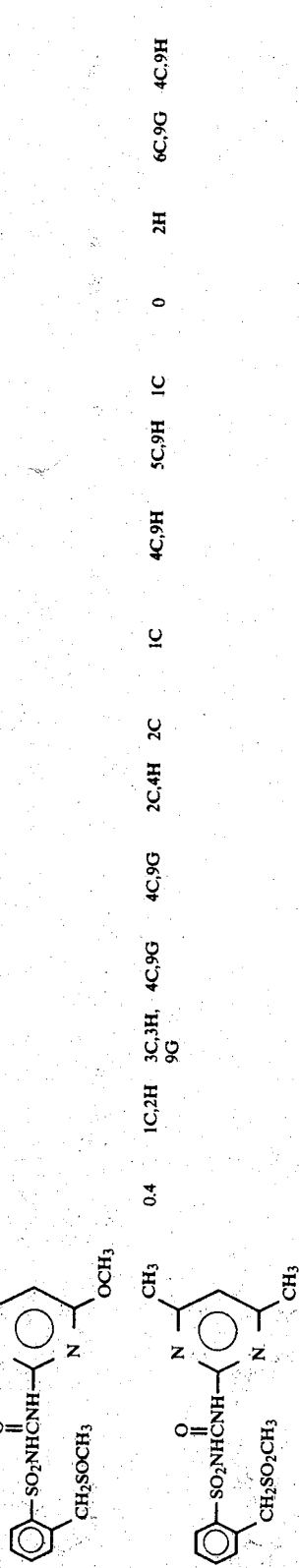 | 0.4 | 1C,2H | 3C,3H, 9G | 4C,9G | 4C,9G | 2C,4H | 2C | 1C | 4C,9H | 5C,9H | 1C | 0 | 2H | 6C,9G | 4C,9H |
| 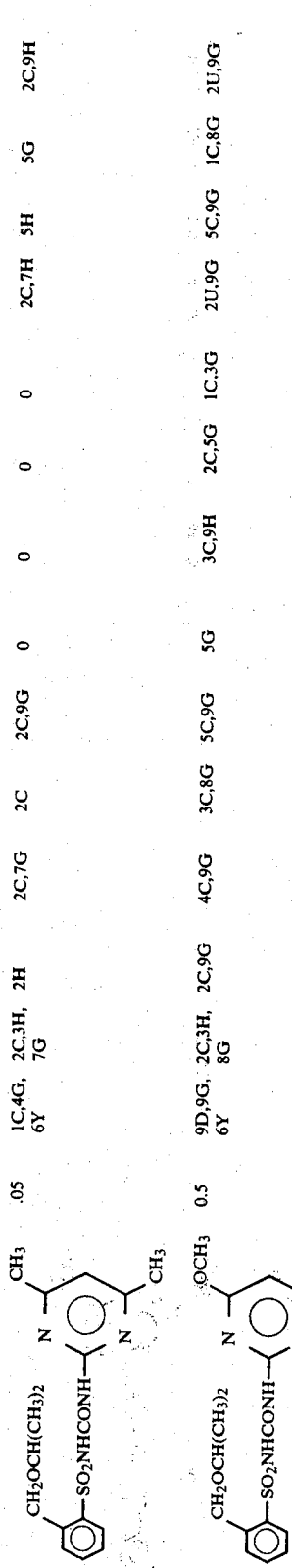 | .05 | 1C,4G, 6Y | 2C,3H, 7G | 2H | 2C,7G | 2C | 2C,9G | 0 | 0 | 0 | 0 | 0 | 2C,7H | 5H | 2C,9H |
| 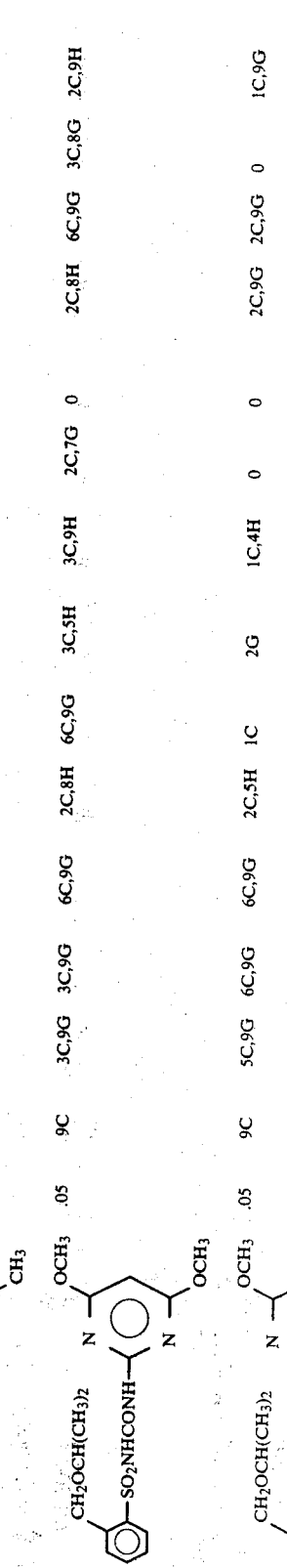 | 0.5 | 9D,9G, 6Y | 2C,3H, 8G | 2C,9G | 4C,9G | 3C,8G | 5G | 5G | 3C,9H | 2C,5G | 1C,3G | 2U,9G | 5C,9G | 1C,8G | 2U,9G |
|  | .05 | 9C | 3C,9G | 3C,9G | 6C,9G | 2C,8H | 6C,9G | 3C,5H | 3C,9H | 2C,7G | 0 | 2C,8H | 6C,9G | 3C,8G | 2C,9H |
|  | .05 | 9C | 5C,9G | 6C,9G | 6C,9G | 2C,5H | 1C | 2G | 1C,4H | 0 | 0 | 2C,9G | 2C,9G | 0 | 1C,9G |

TABLE A-continued

| Structure | Rate | | | | | | | | | | | |
|---|---|---|---|---|---|---|---|---|---|---|---|---|
| ![structure with CH₂SOCH₃, SO₂NHCONH, CH₃, CH₃ on pyrimidine] | .05 | 0 | 0 | 0 | 0 | 0 | 0 | 0 | 0 | 0 | 0 | 0 |
| ![structure with CH₂SOCH₃, SO₂NHCONH, OCH₃, CH₃] | 0.4 | 3C,9G, 6Y | 2C,2H, 7G | 2C | 0 | 1C | 1C | 0 | 0 | 2C,9H | 1C,6H | 2C,8G | 2C,8H |
| ![structure with CH₂SOCH₃, SO₂NHCONH, OCH₃, OCH₃] | 0.4 | 4S,9G, 6Y | 1C,2G | 1C | 0 | 0 | 0 | 1C,2H | 0 | 2C,9H | 1C,5H | 2C,8G | 2C,6H |
| ![structure with CH₂SO₂CH₃, SO₂NHCONH, OCH₃, CH₃] | 0.05 | 3C,7G, 6Y | 0 | 4G | 0 | 4G | 3G | 1H | 0 | 2C,7H | 1H | 2G | 2C,9H |
| ![structure with CH₂SO₂CH₃, SO₂NHCONH, OCH₃, OCH₃] | 0.05 | 2C,6G, 6Y | 2G | 1H,3G | 0 | 0 | 0 | 0 | 0 | 1C,5H | 4H | 2G | 1C,6H |

TABLE A-continued

| Structure | Rate | | | | | | | | | | | | | | |
|---|---|---|---|---|---|---|---|---|---|---|---|---|---|---|---|
| CH₂OCH₂CH₃—C₆H₄—SO₂NHCONH—pyrimidine(CH₃, CH₃) | .05 | 9C | 6C,9G | 3C,7G | 9C | 3C,9G | 9C | 2C,5G | 6C,9H | 9H | 2C,9G | 3C,9G | 2C,9G, 5X | 3C,9G | 4U,9G |
| CH₂OCH₂CH₃—C₆H₄—SO₂NHCONH—pyrimidine(OCH₃, CH₃) | .05 | 9C | 9C | 5C,9G | 9C | 6C,9G | 9C | 2C,7G | 9C | 2C,9G | 2C,9G | 5U,9G | 4C,9G | 3C,9G | 3C,9G |
| CH₂OCH₂CH₃—C₆H₄—SO₂NHCONH—pyrimidine(OCH₃, OCH₃) | .05 | 9C | 6C,9G | 9C | 9C | 2C,9G | 9C | 1C,3G | 4C,9H | 0 | 2C,9G | 2U,9G | 4C,9G | 2C,9G | 1U,9G |
| CH₂OCH₂CH₃—C₆H₄—SO₂NHCONH—triazine(OCH₃, CH₃) | .05 | 9C | 9C | 10C | 9C | 5C,9G | 9C | 1C,2G | 3C,9H | 4G | 0 | 5U,9G | 4C,9G | 6G | 2U,9G |
| CH₂OCH₂CH₃—C₆H₄—SO₂NHCONH—triazine(OCH₃, OCH₃) | .05 | 9C | 9C | 9C | 9C | 5C,9G | 2C,8G, 5X | 1C | 1C,3G | 0 | 0 | 2C,9H | 3H,9G, 7X | 6G | 1C,7G |
| CH₂O(CH₂)₃CH₃—C₆H₄—SO₂NHCONH—pyrimidine(CH₃, CH₃) | .05 | 0 | 1C,3H | 1C,6G | 1C,6F | 1C | 1C,8G | 1C,7G | 1C,6H | 6G | 0 | 2C,7H | 2H,8G | 5G | 2C,9G |

TABLE A-continued

| Structure | Rate | | | | | | | | | | | |
|---|---|---|---|---|---|---|---|---|---|---|---|---|
| CH₂O(CH₂)₃CH₃ / SO₂NHCONH- phenyl; pyrimidine with OCH₃, CH₃ | .05 | 6S,9G, 6Y | 3C,7G | 2C,6G | 3C,9H | 2C,5G | 4G | 2C,8G | 2C,8H | 1C,6G | 1G | 1U,9G | 3C,9G | 8G | 3C,9H |
| CH₂O(CH₂)₃CH₃ / SO₂NHCONH- phenyl; pyrimidine with OCH₃, OCH₃ | .05 | 2C,9G, 6Y | 1C,5G | 1C,5G | 1C,9G | 1C,3G | 1C,7G | 1C,5G | 2C,9H | 2G | 0 | 2C,7G | 2C,8G | 2C,8G | 3C,9G |
| CH₂O(CH₂)₃CH₃ / SO₂NHCONH- pyrimidine with N, CH₃, N, CH₃ | .05 | 2C,5G, 6Y | 1C,1H | | 2C,9G | 1C | 0 | 0 | 0 | 0 | 0 | 2C,8H | 2C,9H | 0 | 2C,9G |
| CH₂O(CH₂)₃CH₃ / SO₂NHCONH- pyrimidine with N, N, OCH₃ | 0.05 | 5S,9G, 6Y | 2C,5G | 1C,7G | 3G,6F | 3C | 0 | 0 | 0 | 0 | 0 | 2G | 1C,9G | 0 | 2C,8G |
| CH₂OCH(CH₃)CH₂CH₃ / SO₂NHCONH- phenyl; pyrimidine with CH₃, OCH₃ | 0.05 | 2C | 4G | 2C,7G | 1C,3G | 2C | 2C,8G | 2H | 0 | 0 | 0 | 2C,7H | 1C,8G | 1C,3G | 2C,9G |

TABLE A-continued

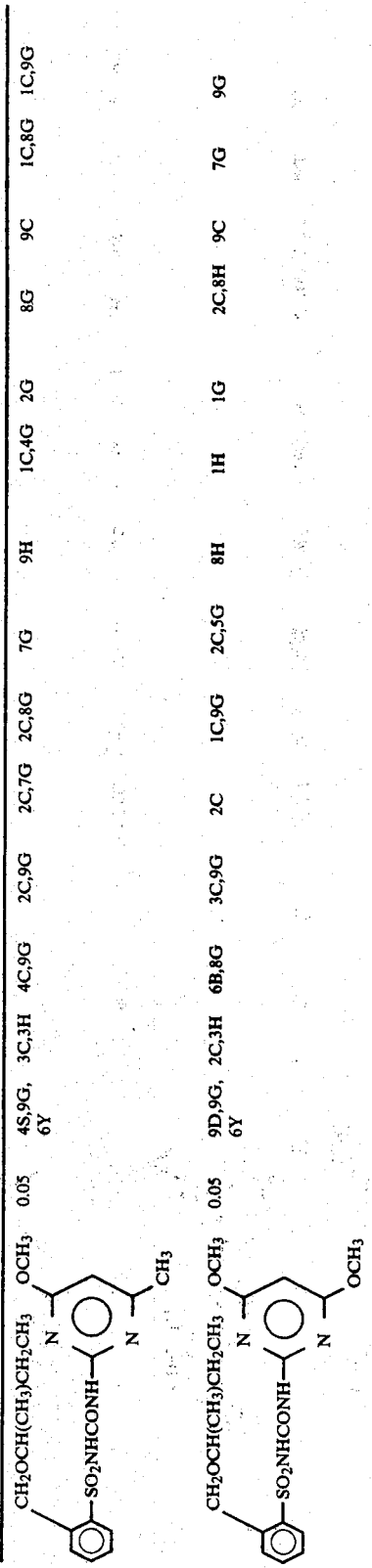

| | kg/ha | MORN-ING-GLORY | COCK-LE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|
| | 0.05 | 4S,9G, 6Y | 4C,9G | 2C,9G | 2C,7G | 2C,8G | | 7G | 9H | 1C,4G | 2G | 8G | 9C | 1C,8G | 1C,9G |
| | 0.05 | 9D,9G, 6Y | 6B,8G | 3C,9G | 2C | 1C,9G | 2C,5G | | 8H | 1H | 1G | 2C,8H | 9C | 7G | 9G |
| | 0.05 | 3C,9G, 6Y | 10C | 1C,2G | 0 | 0 | 0 | 0 | 0 | 0 | 0 | 1C,6G | 2C,8G | 0 | 2G |

PRE-EMERGENCE

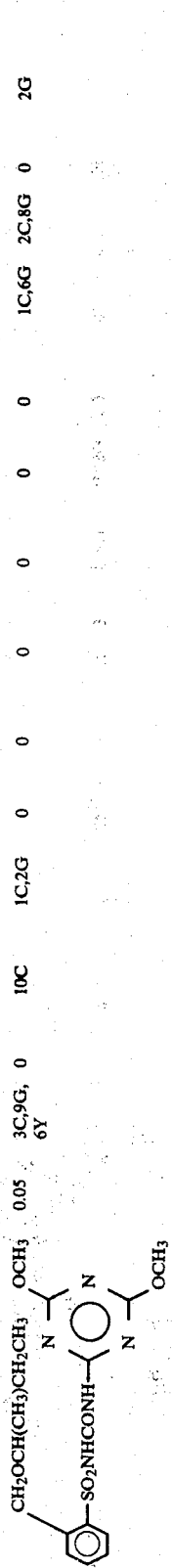

| | kg/ha | MORN-ING-GLORY | COCK-LE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|
| | 0.4 | 9C | | | 10E | 2C,9G | 5C,9H | 4C,9H | 9H | 10E | 9H | 10E | 6C,9H |
| | 0.4 | 9C | 9G | 3C,9G | 10E | 3C,9G | 6C,9H | 5C,9H | 10H | 10E | 9H | 10E | 10H |

TABLE A-continued

| Structure | | | | | | | | | | | | | |
|---|---|---|---|---|---|---|---|---|---|---|---|---|---|
| Structure with SO2NHCNH, CH2OCH3, OCH3/OCH3 pyrimidine | 0.4 | 9G | 9H | 2C,9G | 10E | 2C,9G | 7C,9H | 1C,9G | 9G | 9H | 9H | 10E | 6C,9H |
| Structure with SO2NHCNH, CH2OCH3, CH3/CH3 pyrimidine | 0.4 | 9C | 9H | 5C,9G | 10E | 2C,8G | 6C,9H | 6C,9H | 9G | 9H | 9H | 10E | 10H |
| Structure with SO2NHCNH, CH2OCH3, CH3/OCH3 pyrimidine | 0.4 | 9C | 9G | 2C,9G | 1C,9G | 3C,8G | 5C,9H | 5C,9H | 1C,9G | 9H | 9H | 10E | 3C,9H |
| Structure with SO2NHCNH, CH2OCH3, OCH3/OCH3 pyrimidine | 0.4 | 9C | 9H | 2C,9G | 9G | 3C,5G | 3C,9H | 1C,8G | 5G | 9H | 9H | 10E | 9H |
| Structure with SO2NHCNH, CH2SCH3, CH3/CH3 pyrimidine | 0.4 | 9C | 9H | 3C,7H | 9G | 2C,6G | 2C,9H | 3C,9G | 9G | 2C,9H | 2C,2H | 10E | 2C,9G |
| Structure with SO2NHCNH, CH2SCH3, CH3/OCH3 pyrimidine | 0.4 | 9C | 9H | 4C,9G | 10E | 5C,9G | 6C,9H | 4C,9G | 3C,9G | 10H | 8H | 10E | 7C,9H |

TABLE A-continued

| Structure | | | | | | | | | | | | | |
|---|---|---|---|---|---|---|---|---|---|---|---|---|---|
| Pyrimidine with OCH₃, OCH₃; SO₂NHCNH, phenyl-CH₂SCH₃ | 0.4 | 9C | 9H | 9C | 10E | 6C,9H | 6C,9H | 4C,9G | 9G | 10H | 9H | 10E | 6C,9H |
| Pyrimidine with CH₃, CH₃; SO₂NHCNH, phenyl-CH₂SCH₃ | 0.4 | 5G | 5H | 6C | 0 | 0 | 0 | 0 | 0 | 0 | 0 | 0 | 0 |
| Pyrimidine with CH₃, OCH₃; SO₂NHCNH, phenyl-CH₂SCH₃ | 0.4 | 9G | 9H | 8G | 0 | 2C,7H | 7G | 2G | 9H | | 5H | | 2C,9G |
| Pyrimidine with OCH₃, OCH₃; SO₂NHCNH, phenyl-CH₂SCH₃ | 0.4 | 7G | 9H | 5G | 0 | 6H | 3G | 0 | 1C,8G | 1C,3H | 1C,9H | | 3C |
| Pyrimidine with CH₃, CH₃; SO₂NHCNH, phenyl-CH₂SOCH₃ | 0.4 | 8H | 10H | 2C,5G | 2C,8H | 2C | 6G | 4G | 3C,8H | 2C | 9H | | 5C,8G |

TABLE A-continued

| Structure | | | | | | | | | | | | |
|---|---|---|---|---|---|---|---|---|---|---|---|---|
| Pyrimidine with CH₃, OCH₃; SO₂NHCNH; CH₂SO₂CH₃ | 0.4 | 9G | 9H | 6C,9G 10E | 5C,9G | 6C,9H | 4C,7G | 2C,7G | 6C,9G | 9H | 6C,9H |
| Pyrimidine with CH₃, OCH₃; SO₂NHCNH; CH₂SOCH₃ | 0.4 | 9C | 9H | 5C,8G 10E | 5C,9G | 5C,9H | 5C,8G | 1C,9G | 3C,9G | 8H | 10E | 6C,9H |
| Pyrimidine with OCH₃, OCH₃; SO₂NHCNH; CH₂SO₂CH₃ | 0.4 | 10C | 9H | 6C,9G 10E | 2C,7G | 5C,9H | 2C,8G | 0 | 5C,9H | 9H | 10E | 10H |
| Pyrimidine with OCH₃, OCH₃; SO₂NHCNH; CH₂SOCH₃ | 0.4 | 4C,9G | 9H | 5C,9G 10E | 5C,9G | 6C,9H | 5C,8G | 9G | 10H | 9H | 10E | 10H |
| Pyrimidine with CH₃, CH₃; SO₂NHCNH; CH₂SO₂CH₃ | 0.4 | 8H | 9H | 2C | 0 | 1C,6H | 9G | 0 | 2C,6H | 2C | 2C,9H | 4C,9H |
| Pyrimidine with CH₃, CH₃; SO₂NHCONH; CH₂OCH(CH₃)₂ | .05 | 6G | 9H | 2C,5H 2G | 0 | 1H | 2C,5G | 1C,4G | 2C,8H | 2C | 2C,6G | 1C,7H |

TABLE A-continued

| Structure | | | | | | | | | | | | |
|---|---|---|---|---|---|---|---|---|---|---|---|---|
| Structure with CH₂OCH(CH₃)₂, SO₂NHCONH-, OCH₃, CH₃ | .05 | 9G | 9H | 1C,9G | 9G | 3G | 4C,9H | 4C,9G | 1C,9G | 10H | 9H | 2C,8G 2C,9H |
| Structure with CH₂OCH(CH₃)₂, SO₂NHCONH-, OCH₃, OCH₃ | .05 | 9G | 9H | 9G | 10E | 2C,5G | 3C,9H | 1C,7G | 3G | 2C,9H | 9H | 4C,8H 2C,9H |
| Structure with CH₂OCH(CH₃)₂, SO₂NHCONH-, OCH₃, CH₃ | .05 | 2C,9G | 2C,9H | 5C,9G | 5G | 0 | 7H | 0 | 0 | 3C,9G | 2C,8H | 2C,5G 2C,9H |
| Structure with CH₂SOCH₃, SO₂NHCONH-, CH₃, CH₃ | .05 | 10E | 0 | 0 | 0 | 0 | 0 | 0 | 0 | 0 | 0 | 0 |
| Structure with CH₂SOCH₃, SO₂NHCONH-, CH₃, CH₃ | | | | 5C | 0 | 0 | 1C | 0 | 0 | 0 | 0 | 0 |
| Structure with CH₂SOCH₃, SO₂NHCONH-, OCH₃, CH₃ | 0.4 | 2C,6H | 9H | | | | | | | 2C,8H | 1C,3G | 2C,5G 2C,9H |

TABLE A-continued

| Structure | | | | | | | | | | | | | |
|---|---|---|---|---|---|---|---|---|---|---|---|---|---|
| Phenyl with CH₂SOCH₃ and SO₂NHCONH-pyrimidine(OCH₃, OCH₃) | 0.4 | 1C | 0 | 0 | 0 | 1C,2H | 0 | 2C,8H | 2C | 1C,5G | 1C,7G |
| Phenyl with CH₂SO₂CH₃ and SO₂NHCONH-pyrimidine(OCH₃, CH₃) | 0.05 | 0 | 0 | 0 | 0 | 0 | 0 | 9H | 1C | 0 | 2C,4G |
| Phenyl with CH₂SO₂CH₃ and SO₂NHCONH-pyrimidine(OCH₃, OCH₃) | 0.05 | 0 | 0 | 0 | 0 | 0 | 0 | 3G | 1C | 3G | 2C |
| Phenyl with CH₂OCH₂CH₃ and SO₂NHCONH-triazine(CH₃, CH₃) | .05 | 9G | 9H | 1C,9G | 10E | 1C,4G | 2C,9H | 0 | 3G | 1C | 10E | 5C,9G |
| Phenyl with CH₂OCH₂CH₃ and SO₂NHCONH-triazine(OCH₃, CH₃) | .05 | 9G | 9H | 2C,9G | 10E | 2C,6G | 6C,9H | 3C,9G | 9G | 1C,9G | 2C,3G | 10E |
| Phenyl with CH₂OCH₂CH₃ and SO₂NHCONH-triazine(OCH₃, OCH₃) | .05 | 9G | 9H | 2C,9G | 10E | 2C,6G | 3C,9H | 2C,9H | 2C,9G | 9H | 9H | 3C,9H |
| Phenyl with CH₂OCH₂CH₃ and SO₂NHCONH-pyrimidine(OCH₃, CH₃) | .05 | 9G | 9H | | | | 2C,9H | 2C,7G | 2U,9G | 9H | 4C,9H | 2C,9G |

TABLE A-continued

| Structure | | | | | | | | | | | | | |
|---|---|---|---|---|---|---|---|---|---|---|---|---|---|
| Benzene with CH$_2$OCH$_2$CH$_3$ and SO$_2$NHCONH—[pyrimidine: OCH$_3$, CH$_3$] | .05 | 9G | 9H | 3C,9G | 6G | 1C | 2C,8H | 5G | 2G | 9G | 8H | 8H | 2C,9G |
| Benzene with CH$_2$OCH$_2$CH$_3$ and SO$_2$NHCONH—[pyrimidine: OCH$_3$, OCH$_3$] | .05 | 9G | 9H | 2C,9G | 8G | 1C,2G | 2C,8H | 1C,3G | 0 | 2C,9H | 7H | 6G | 2C,8G |
| Benzene with CH$_2$O(CH$_2$)$_3$CH$_3$ and SO$_2$NHCONH—[pyrimidine: CH$_3$, CH$_3$] | .05 | 0 | 0 | 1C | 0 | 1C | 1C,5G | 2C,7G | 3G | 2C,7G | 1C | 2C | 2C,6G |
| Benzene with CH$_2$O(CH$_2$)$_3$CH$_3$ and SO$_2$NHCONH—[pyrimidine: OCH$_3$, CH$_3$] | .05 | 1H,7G | 9H | 2C,6G | 1C,7G | 1C | 2C,9H | 2C,8G | 1C,8G | 2C,9G | 9H | 4C,9H | 2C,9H |
| Benzene with CH$_2$O(CH$_2$)$_3$CH$_3$ and SO$_2$NHCONH—[pyrimidine: OCH$_3$, OCH$_3$] | .05 | 1C | 5H | 2C,3G | 9G | 2C | 3C,9H | 2C,7G | 5G | 2C,8G | 5G | 2C,9H | 2C,9G |

TABLE A-continued

| Structure | Rate | | | | | | | | | | | |
|---|---|---|---|---|---|---|---|---|---|---|---|---|
| CH₂O(CH₂)₃CH₃—phenyl-SO₂NHCONH—pyrimidine(OCH₃, CH₃) | .05 | 9G | 9H | 0 | 0 | 0 | 1C,5G | 0 | 0 | 2C,7G | 1C | 2C | 3C,9H |
| CH₂O(CH₂)₃CH₃—phenyl-SO₂NHCONH—pyrimidine(OCH₃, OCH₃) | 0.05 | 8G | 9H | 1C | 0 | 0 | 1C | 0 | 0 | 1C,3G | 3G | 2C | 2C,8G |
| CH₂OCH(CH₃)CH₂CH₃—phenyl-SO₂NHCONH—pyrimidine(CH₃, CH₃) | 0.05 | 2G | 9H/0 | 5G | 4G | 3C,6G | 1C,6G | 3G | 2C,6G | 1C,1H | 3C,7G | 1C,8G | |
| CH₂OCH(CH₃)CH₂CH₃—phenyl-SO₂NHCONH—pyrimidine(OCH₃, CH₃) | 0.05 | 9G | 9H | 1C,7G | 9G | 2C,6G | 1C,9H | 8G | 8G | 9G | 9H | 4C,9H | 2C,9H |
| CH₂OCH(CH₃)CH₂CH₃—phenyl-SO₂NHCONH—pyrimidine(OCH₃, CH₃) | 0.05 | 8G | 8H | 2C,8G | 0 | 2C,5G | 2C,8H | 2C,6G | 1C,3G | 2C,9H | 9H | 5C,9H | 9G |
| CH₂OCH(CH₃)CH₂CH₃—phenyl-SO₂NHCONH—pyrimidine(OCH₃, OCH₃) | 0.05 | 9G | 9H | 1C | 0 | 0 | 1C | 0 | 0 | 1C,5G | 2H | 1C,4G | 3C,8H |

The following compounds

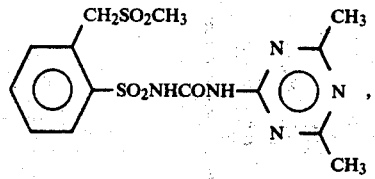

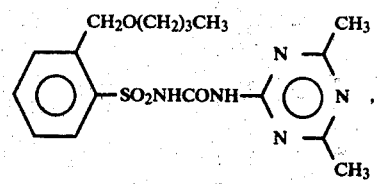

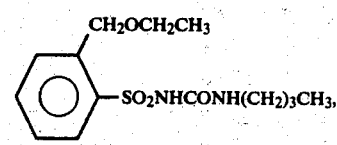

and

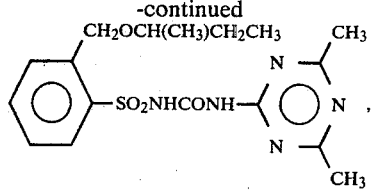

demonstrated virtually no activity when tested at low levels. It is thought they would be herbicidally active when tested at higher levels.

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot ws also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

TABLE B
PRE-EMERGENCE ON FALLSINGTON SILT LOAM SOIL

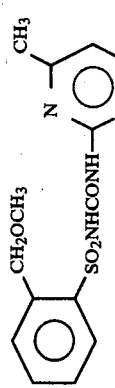

| Rate kg/ha | Crab-grass | Barn-yard-grass | Sor-ghum | Wild Oats | John-son-grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 0 | 8G,5H | 9G,9C | 7G,5H | 8G,4C | 3G | 4G | 7G,3C | 8G | 9G,9C | 5G,2H | 10C | 5G | 9G,9C | 5G | 4G,3H | 3G | 7G | 5G | 8G,5H | 6G | 3G | 10E | 5G,3C |
| 0.12 | 7G,3C | 10C | 10E | 9G,9H | 9G,9C | 7G,5C | 5G | 10C | 10E | 10C | 9G,9C | 10C | 7G | 10E | 5E,9G | 8G | 7G | 9G,8C | 7G,3C | 9G,8C | 7G | 6G,5H | 10E | 7G,7C |

| Rate kg/ha | Crab-grass | Barn-yard-grass | Sor-ghum | Wild Oats | John-son-grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.01 | 0 | 5G | 2G | 0 | 3G | 2G | 3G | 4G | — | 5G | 0 | 8G,7C | 0 | 0 | 0 | 0 | 3G | 0 | 0 | 0 | 0 | 0 | 5G | 0 |
| 0.015 | 3G | 7G,3H | 7G,3H | 5G | 6G,3H | 2G | 9E | 7G,5E | 5G | 10C | 5G | 9G,8C | 0 | 3G | 0 | 0 | 3G | 6G | 3G | 2G | 4G | 3G | 7G,3H | 0 |
| 0.03 | 5G | 9G,8C | 10C | 5G,3C | 8G,5H | 3G | 6G | 7G,5C | 7G | 10C | 7G,5H | 10C | 3G | 10E | 5G | 7G,3H | 6G | 9G,6C | 5G | 9G | 8G,8C | 7G,5H | 8G,7C | 5G,3C |
| 0.12 | 7G,3C | 9G,9C | 10C | 9G,9C | 9G,5C | 8G,8C | 9G,9C | 10C | 10E | 10C | 10C | 10C | 8G | 10E | 8G | 8G,4C | 9G | 9G,8C | 7G,5C | 9G,8C | 9G,9C | 9G,8C | 10E | 6G,3C |

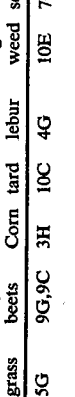

| Rate kg/ha | Crab-grass | Barn-yard-grass | Sor-ghum | Wild Oats | John-son-grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 2G | 7G,5H | 8G,5H | 5G,3H | 6G | 0 | 0 | 8G,8C | 5G | 9G,9C | 3H | 10C | 4G | 10E | 7G | 6G | 3G | 8G | 4G | 8G,3H | 8G,8C | 4G,3H | 8G,5C | 3G |

TABLE B-continued
PRE-EMERGENCE ON FALLSINGTON SILT LOAM SOIL

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.12 | 5G | 10C | 10C | 6G,4C | 7G,5H | 5G | 7G,7C | 10C | 7G,3C | 10C | 9G,9C | 10C 7G | 10E | 8G,4C | 7G,5H | 9G,3C | 3G | 7G,3C | 9G,9C | 9G,8C | 7G,5H | 10C 3G |

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 0 | 3G | 8G,3H | 3G | 6G | 0 | 0 | 4G,3C | 0 | 9G,9C | 3H | 10C | 4G | 9G,8C | 0 | 3G | 3G | 3G | 3G | 7G | 6G | 4G | 7G,3C | 0 |
| 0.12 | 5G | 5G,3H | 9G,8C | 7G,4C | 8G,5H | 0 | 2G | 8G,8C | 5G | 10C | 7G,3H | 10C | 6G,3H | 9G,9C | 5G | 7G,5H | 6G | 8G | 7G,5H | 9G,5C | 9G,9C | 7G,5H | 10E | 3G |

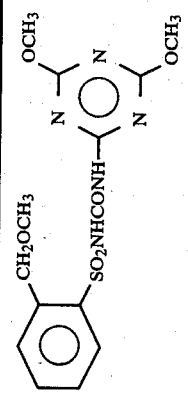

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 0 | 4G | 9G,9C | 6G,2C | 6G | 0 | 0 | 7G,6C | 0 | 10C | 7G,5H | 10C | 6G | 10E | 5G | 8G,5H | 8G | 9G,3C | 7G,3C | 9G,5C | 9G,9C | 8G,5H | 6G,3C | 0 |
| 0.12 | 6G | 7G,5G | 10C | 6G,4C | 7G,3H | 5G | 6G | 8G,9C | 6G,3C | 10C | 8G,9C | 10C | 7G,5H | 10E | 7G | 9G,5C 3C | 9G,8C | 8G,8C | 8G,5C | 9G,7C | 10C | 9G,8C | 7G,6C | 3G |

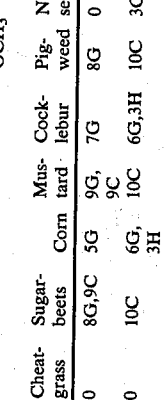

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 0 | 2G | 6G,3H | 0 | 0 | 0 | 0 | 3G | 0 | 8G,9C | 5G | 9G,9C | 7G | 8G | 0 | 7G,3H | 8G,5H | 9G,4C | 6G,3C | 8G,5H | 7G,4C | 7G,5H | 6G | 0 |
| 0.12 | 0 | 5G | 8G,5H | 4G | 6G,3H | 3G | 0 | 6G | 0 | 10C | 6G,3H | 10C | 6G,3H | 10C | 3G | 8G | 9G,3C | 9G,6C | 7G,3C | 9G,7C | 9G,7C | 8G,5H | 7G | 0 |

TABLE B-continued
PRE-EMERGENCE ON FALLSINGTON SILT LOAM SOIL

Compound 1: phenyl ring with CH₂SCH₃ ortho, SO₂NHCONH-pyrimidine (CH₃, OCH₃ substituents)

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 0 | 4G | 6G,3H | 2G | 5G | 0 | 5G | 5G | 10E | 6G,5C | 0 | 9G,8C | 3G | 6G | 5G | 3G | 2C | 3G | 3G | — | 3G | 4G,3H | 6G | 2G |
| 0.12 | 3G | 7G | 10C | 5G,5C | 8G,5H | 4G | 7G | 7G,5C | 8G,9C | 9G,9C | 4G | 9G,8C | 5G | 8G | 7G | 4G | 8G,5H | 5G,3H | 7G | 5G,3H | 8G,5H | 5G,5H | 7G,3H | 4G |

Compound 2: phenyl ring with CH₂SCH₃ ortho, SO₂NHCONH-pyrimidine (OCH₃, OCH₃ substituents)

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 2G | 8G,5H | 10C | 5G | 9G,9C | 3G | 8G,5H | 6G,3C | 7C | 8G,8C | 6G,3H | 10C | 4G | 8G,5C | 7G | 6G,3H | 6G,3H | 7G,5H | 4G | 8G,5H | 8G,5H | 5G,5H | 10E | 3G |
| 0.12 | 6G,3H | 9G,9C | 10E | 5G,5C | 10C | 8G,8C | 10C | 10C | 10E | 10C | 8G,8C | 10C | 7G,7C | 10C | 10C | 8G,5H | 8G,5H | 8G,7C | 8G,5H | 8G,5H | 9G,6C | 7G,5H | 10E | 5G |

Compound 3: phenyl ring with CH₂SO₂CH₃ ortho, SO₂NHCONH-pyrimidine (CH₃, OCH₃ substituents)

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 0 | 4G | 10C | 3G | 6G, | — | 5G | 6G | — | 8G,9C | 3G | 9G,9C | 6G,2C | 0 | 4G | 4G,5H | 4G,3H | 2C | 3G,2C | 2C | 5G,5H | 4G,5H | 6G | 2G |
| 0.12 | 0 | 7G,8C | 9G,9C | 5G | 7G,3H | — | 7G,3H | 7G,5C | — | 10C | 9G,8C | 10C | 6G,5H | 6G | 6G | 6G,5H | 8G,5H | 5G,3C | 5G,3H | 8G,5H | 7G,5C | 6G,5H | 8G,5C | 3G |

TABLE B-continued
PRE-EMERGENCE ON FALLSINGTON SILT LOAM SOIL

Structure 1: phenyl with CH₂S(O)CH₃ ortho to SO₂NHCONH-pyrimidine (4-CH₃, 6-OCH₃)

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 0 | 4G | 9G,9C | 3G | 4G,2H | — | 3G | 5G | — | 7G,8C | 9G,9C | 9G,9C | 4G | 3G | 4G | 3G | 4G,3H | 2G | 2G | 4G | 3G | 3G | 6G | 2G |
| 0.12 | 3G | 7G,8C | 10C | 7G,3H | 9G,8C | — | 6G,3H | 7G,5C | — | 10C | 4G,3H | 10C | 7G,3H | 8G,8C | 9G,8E | 5G,3H | 7G,5H | 6G,3C | 3G,2C | 6G,5H | 8G,5H | 5G,3H | 8G,5C | 4G |

Structure 2: phenyl with CH₂SO₂CH₃ ortho to SO₂NHCONH-pyrimidine (4-OCH₃, 6-OCH₃)

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 3G | 8G,8C | 10C | 2G | 7G,3H | — | 5G | 6G | — | 10C | 7G,5H | 10C | 3G | 8G,8C | 10E | 6G,5H | 4G,3H | 7G,5C | 3G,2C | 7G,5H | 8G,7C | 6G,5H | 7G | 0 |
| 0.12 | 3G | 10C | 10C | 4G | 9G,9C | — | 8G,3H | 7G,3C | — | 10C | 9G,9C | 10C | 7G,5H | 9G,8C | 10E | 6G,5H | 8G,5H | 8G,6C | 5G,3H | 8G,5H | 8G,5C | 7G,5H | 8G,5C | 2G |

Structure 3: phenyl with CH₂S(O)CH₃ ortho to SO₂NHCONH-pyrimidine (4-OCH₃, 6-OCH₃)

| Rate kg/ha | Crab-grass | Barn-yard-grass | Sor-ghum | Wild Oats | John-son grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.03 | 3G | 7G,8C | 10C | 5G | 9G,8C | — | 7G,3H | 7G,5C | — | 10C | 6G,5H | 9G,9C | 4G | 8G,7C | 6G | 4G | 6G,3H | 7G | 0 | 6G,5H 5H | 7G,5H | 8G,7C | 8G | 3G |
| 0.12 | 9G,8C | 10C | 10C | 8G,8C | 10C | — | 10C | 10C | — | 10C | 10C | 10C | 8G,5H | 10C | 10E | 8G,5H | 8G,5H | 9G,8C | 6G,5H | 8G,3H | 8G,7C | 8G,5H | 10C | 5G |

TABLE B-continued
PRE-EMERGENCE ON FALLSINGTON SILT LOAM SOIL
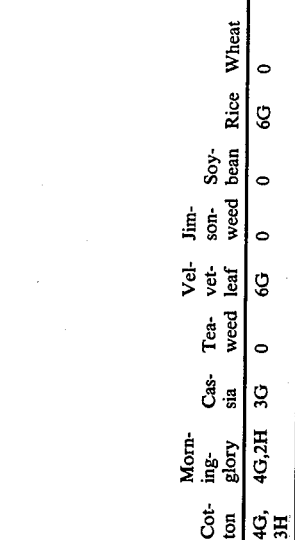
| Rate kg/ha | Crab-grass | Barn-yard-grass | Sor-ghum | Wild Oats | John-son-grass | Dal-lis-grass | Giant foxtail | Ky. blue-grass | Cheat-grass | Sugar-beets | Corn | Mus-tard | Cock-lebur | Pig-weed | Nut-sedge | Cot-ton | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|---|---|---|---|---|---|---|---|---|---|---|
| 0.25 | 0 | 0 | 7G,5H | 4G | 3G | 0 | 0 | 0 | 4G | 10C | 0 | 9G,9C | 0 | 0 | 0 | 4G,3H | 4G,2H | 3G | 0 | 6G | 0 | 0 | 6G | 0 |

TEST C

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (*Digitaria* spp.), nutsedge (*Cyperus rotundus*), barnyardgrass (*Echinochloa crusgalli*), giant foxtail (*Setaria faberii*) and wild oats (Avena fatua). Approximately two weeks after planting, the young plants and the soil around them were sprayed overall with the test chemicals dissolved in a non-phytotoxic solvent. Two weeks after treatment, all species were compared to untreated controls and visually rated for response to treatment. The rating system was as described previously for Test A. The data are presented in Table C. Several of the compounds tested by this procedure are useful for the post-emergence control of weeds in wheat.

TABLE C

| Compound | Rate kg/ha | Soybeans | Velvetleaf | Sesbania | Cassia | Cotton | Morningglory | Alfalfa | Jimsonweed | Cocklebur | Corn | Crabgrass | Rice | Nutsedge | Barnyardgrass | Wheat | Giant Foxtail | Wild Oats | Sorghum |
|---|---|---|---|---|---|---|---|---|---|---|---|---|---|---|---|---|---|---|---|
| Ph(CH₂OCH₃)SO₂NHCONH—pyrimidine(CH₃,CH₃) | 0.06 | 10G,7C | 9C | 10C | 10G,7C | 9G,4C | 10G,5C | 6G,2C | — | 7C,10G | 8G,4U | 3G,1C | 8G,3C | 8G,3C | 8G,4C | 6G | 3G,1C | 7G,2C | 8G,4C |
|  | 0.015 | 10G,5C | 9C | 10G,9C | 10G,4C | 7G,3C | 3G | 2G | 3G,2C | 4G | 5G,3H | 1C | 8G,2C | 3G,2C | 8G | 1G | 0 | 5G | 8G,2C |
| Ph(CH₂OCH₃)SO₂NHCONH—pyrimidine(CH₃,OCH₃) | 0.06 | 10G,9C | 10C | 10C | 10G,8C | 9C | 10C | 9C | — | 8G,3C | 9G,7C | 6G,1C | 10G,5C | 9G,6C | 8G,4C | 8G,2C | 8G | 9G,3C | 9G,3C |
|  | 0.015 | 10G,8C | 9C | 10C | 10G,7C | 9C | 10C | 9G,6C | — | 5G,3C | 8G,4U | 3G | 10G,5C | 7G | 8G,2C | 6G,2C | 6G,1C | 8G,2C | 9G,2C |
| Ph(CH₂OCH₃)SO₂NHCONH—pyrimidine(OCH₃,OCH₃) | 0.06 | 10G,7C | 10C | 10G,9C | 10G,8C | 10G,6C | 10C | 8C | — | 10C | 7G,5H | 3G | 9G,5C | 9G,5C | 3C,8G | 2G,1C | 7G,2C | 0 | 8G,2C |
|  | 0.015 | 10G,8C | 10C | 10G,6C | 10G,7C | 9G,6C | 10C | 10G,7C | — | 1G | 6G,5H | 0 | 10G,5C | 8G | 8G | 1C | 7G | 0 | 4G |
| Ph(CH₂OCH₃)SO₂NHCONH—triazine(CH₃,CH₃) | 0.06 | 10G,7C | 10C | 10C | 10G,7C | 6G,3C | 10C | 8C | — | 10G,6C | 8G,5C | 0 | 9G,5C | 9G,1C | 3C,8G | 0 | 5G | 0 | 8G,3C |
|  | 0.015 | 10G,4C | 10G,8C,5G,1C | 10G,6C | 10G,5C | 5G,3C | 6G,2C | 6G,3C | — | 5G,3C | 8G,4U | 0 | 9G | 8G | 3C,5G | 0 | 5G | 1C | 7G,3C |
| Ph(CH₂OCH₃)SO₂NHCONH—triazine(CH₃,OCH₃) | 0.06 | 10G,7C | 10C | 10G,9C,10G,6C | 10G,8C | 10G,7C | 10C | 10C | — | 10G,7C | 8G,5U | 1G | 8G,3C | 1G | 7G,3C | 0 | 4G | 0 | 8G,3C |
|  | 0.015 | 10G,7C | 10C | 10C | 10G,8C | 10G,7C | 10C | 9C | 5G,2C | 10G,7C | 8G,4U | 1G | 9G | 2G | 3G | 0 | 4G,1C | 0 | 7G,3C |

TABLE C-continued

| Structure | Rate kg/ha | Soy-beans | Vel-vet-leaf | Ses-bania | Cas-sia | Cot-ton | Morn-ing-glory | Al-fal-fa | Jim-son-weed | Cock-lebur | Corn | Crab-grass | Rice | Nuts-edge | Barn-yard-grass | Wheat | Giant Fox-tail | Wild Oats | Sor-ghum |
|---|---|---|---|---|---|---|---|---|---|---|---|---|---|---|---|---|---|---|---|
| CH$_2$SCH$_3$ phenyl—SO$_2$NHCONH—pyrimidine(CH$_3$, OCH$_3$) | 0.25 | 9G,6C | 9G,5C | 4C,7G | 8G,4C | 8G,5C | 9G,5C | 4C,9G | — | 10G,5C | 8G,8U | 6G,3C | 9G,6C | 7G,1C | 10C | 5G,2C | — | 7G,4C | 8G,5C |
|  | 0.06 | 7G,4C | 7G,3C | — | 5G,3C | 7G,3C | 7G,4C | 4C,9G | — | 10G,5C | 7G,7U | 5G | 8G,5C | 3G | 8G,5C | 4G | — | 7G,4C | 8G,4C |
| CH$_2$SCH$_3$ phenyl—SO$_2$NHCONH—pyrimidine(OCH$_3$, OCH$_3$) | 0.25 | 10G,7C | 10G,5C | — | 5C,8G | 9G,5C | 9G,6C | 9C | — | 10G,7C | 9G,9U | 8G,6C | 9G,7C | 7G,2C | 10C | 7G,2C | — | 8G,6C | 9G,6C |
|  | 0.06 | 10G,7C | 7G,3C | — | 4C,7G | 4G,2C | 9G,6C | 8C | — | 10G,5C | 7G,9U | 6G,3C | 9C | 5G,2C | 10C | 5G | 10C | 8G,4C | 9G,4C |
| CH$_2$S(O)CH$_3$ phenyl—SO$_2$NHCONH—pyrimidine(CH$_3$, CH$_3$) | 0.12 | 1H | 3G,1C | 1C | 3C | 2C | 7G,3C | 3C,5G | 3G | — | 5G,3C | 5G,1C | 9G,3C | 4G,1C | 9G,3C | 5G | 8G,3C | 8C | 9G,4C |
|  | 0.03 | 1H | 5G,1C | 0 | 0 | 0 | 6G,3C | 3C,5G | — | 0 | 1G,2C | 0 | 9G,2C | 0 | 3G | 0 | 5G,2C | — | 9G,3C |
| CH$_2$SO$_2$CH$_3$ phenyl—SO$_2$NHCONH—pyrimidine(CH$_3$, OCH$_3$) | 0.12 | 10G,7C | 7G,3C | 8G,3C | 9G,5C | 8G,4C | 10G,7C | 8C | — | 10G,7C | 8G,3C | 6G,1C | 8G,3C | 8G,3C | 9G,2C | 2G | 8G,4C | — | 9G,4C |
|  | 0.03 | 10G,6C | 4G,2C | 5G,3C | 6G,4C | 7G,4C | 9G,3C | 7G,3C | — | 9G,3C | 5G,3C | 5G,2C | 5G | 0 | 8G | 0 | 5G,2C | 5G,3C | 9G,4C |
| CH$_2$S(O)CH$_3$ phenyl—SO$_2$NHCONH—pyrimidine(CH$_3$, OCH$_3$) | 0.12 | 10G,6C | 8G,3C | 5G,3C | 8G,6C | 8G,4C | 9G,4C | 7G,3C | — | 10G,6C | 10C | 3C,7G | 8C | 9G | 10C | 7C | 10C | 10C | 10C |
|  | 0.03 | 9G,5C | 5G,3C | 9G,3C | 8G,6C | 6G,3C | 9G,3C | 3C | — | 9G,3C | 8G,5U | 0 | 8G,3C | 3C | 10C | 2G | 10C | 8G,4C | 9G,4C |

TABLE C-continued

| Structure | Rate kg/ha | Soy-beans | Vel-vet-leaf | Ses-bania | Cas-sia | Cot-ton | Morn-ing-glory | Al-fal-fa | Jim-son-weed | Cock-lebur | Corn | Crab-grass | Rice | Nuts-edge | Barn-yard-grass | Wheat | Giant Fox-tail | Wild Oats | Sor-ghum |
|---|---|---|---|---|---|---|---|---|---|---|---|---|---|---|---|---|---|---|---|
| 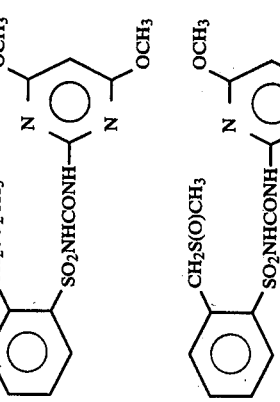 CH$_2$SO$_2$CH$_3$ / SO$_2$NHCONH- pyrimidine with OCH$_3$, OCH$_3$ | 0.03 | 10G, 7C | 7G, 5C | 9G,6C | 10G, 7C | 8G,3C | 9G,4C | 9C | 7G,3C | 10G, 6C | 9G,2C | 0 | 7G | 9G,4C | 8C | 0 | 7G,3C | 1G | 9G,4C |
| 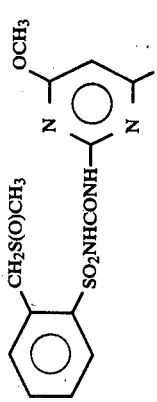 CH$_2$S(O)CH$_3$ / SO$_2$NHCONH- pyrimidine with OCH$_3$, OCH$_3$ | 0.12 | 10G, 7C | 10G, 1C | 10G, 8C | 10G, 7C | 9G,5C | 10G, 8C | 9C | 9G,7C | 10G, 8C | 10C | 7G,3C | 9G, 3C | 10C | 10C | 3G | 10C | 10C | 10C |
|  | 0.03 | 10G, 7C | 9G, 5C | 10G, 8C | 9G,5C | 9G,5C | 10G, 5C | 7C | 5G | 10G, 7C | 9C | 5G | 9G, 3C | 9G,3C | 9C | 1G | 8C | — | 10C |

TEST D

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descurainia pinnata*), smartweed (*Polygonum pennsylvanicum*), tumble mustard (*Sisymbrium altissium*) kochia (*Kochia scoparia*), shepherd's purse (*Capsella bursa-pastoris*), *Matricaria inodora*, black nightshade (*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated in accordance with the rating system described for Test A. The recorded data are presented in Table D. The data indicate that certain compounds from within the scope of this invention have utility for weed control in cereal crops, such as wheat and barley.

TABLE D

| Structure | Rate kg/ha | wheat | barley | wild oats | downy brome | cheatgrass | blackgrass | annual bluegrass | green foxtail | quackgrass | Italian ryegrass | ripgut brome |
|---|---|---|---|---|---|---|---|---|---|---|---|---|
| ![compound with CH2OCH3 and OCH3,OCH3] | | | | | | | Post-emergence | | | | | |
| | 0.06 | 0 | 0 | 0 | 1G | 2G | 2G | 5G | 0 | 0 | 2G | 0 |
| | 0.25 | 0 | 0 | 0 | 5C,4G | 3C,7G | 6G | 3C,6G | 1C,1G | 0 | 1C,3G | 0 |
| | | | | | | | Pre-emergence | | | | | |
| | 0.06 | 0 | 1C,2G | 0 | 2C,2G | 2G | 2C,3G | 5G | 0 | 1C,3G | 3G | 2G |
| | 0.25 | 0 | 2C,2G | 2G | 7C,6G | 7C,8G | 3C,7G | 1C,7G | 3C,4G | 4C,6G | .4C,7G | 3C,4G |
| | | | | | | | Post-emergence | | | | | |
| | 0.25 | 0 | 0 | 0 | 0 | 0 | 2C,4G | 2G | 1C,2G | 1C,1G | 3G | 0 |
| ![compound with CH2SCH3 and CH3,OCH3] | | | | | | | Pre-emergence | | | | | |
| | 0.25 | 0 | 0 | 0 | 2G | 1G | 2G | 3G | 0 | 0 | 0 | 0 |
| | | | | | | | Post-emergence | | | | | |
| | 0.06 | 2C,2G | 7C,6G | 0 | 6C,7G | 5C,6G | 2C,3G | 1C,2G | 1C,1G | 5C,5G | 10C | 7C,7G |
| ![compound with CH2S(O)CH3 and CH3,CH3] | | | | | | | Pre-emergence | | | | | |
| | 0.06 | 0 | 0 | 0 | 2C,3G | 1C,3G | 2C,3G | 1C,5G | 0 | 0 | 0 | 0 |
| | | | | | | | Post-emergence | | | | | |
| | 0.015 | 0 | 0 | 0 | 0 | 0 | 0 | 0 | 0 | 0 | 0 | 0 |
| | 0.06 | 0 | 3G | 0 | 2C,2G | 5C,6G | 7C,8G | 2C,3G | 3C,5G | 1C,2G | 1C | 2G |
| ![compound with CH2SO2CH3 and OCH3,OCH3] | | | | | | | | | | | | |

TABLE D-continued

| Structure | Rate kg/ha | Russian thistle | tansy mustard | smartweed | jimhill mustard | Kochia | shepherd's purse | false chamomile | black nightshade | yellow rocket | wild mustard | wild buckwheat |
|---|---|---|---|---|---|---|---|---|---|---|---|---|
| CH₂S(O)CH₃ —⌬— SO₂NHCONH— pyrimidine(OCH₃)₂ | 0.015 | 1C,1G | 1C | 0 | 2C | 2C,2G | 2C,3G | 7C,8G | 7C,7G | 3G | 1G | 0 | 0 |
| | 0.06 | 6C,5G | 1C,1G | 3G | 1C,2G | 5C,4G | 8C,8G | 7C,8G | 6C,7G | 3C,4G | 1C,6G | 1C,3G |
| | 0.015 | 1C,1G | 3C,2G | | 6C,4G | 10C | 8C,7G | 8C,7G | 8C,7G | 2C,3G | 3C,4G |
| | 0.06 | 6C,5G | 8C,7G | | 10C | 10C | 10C | 10C | 10C | 10C | 10C | 10C |
| CH₂OCH₃ —⌬— SO₂NHCONH— pyrimidine(OCH₃)₂ | 0.015 | 0 | 3G | | 10C | 10C | 7C,7G | 3C,7G | 3C,7G | 5G | 3G | 2G |
| | 0.06 | 0 | 3C,7G | | 10C | 10C | 10C | 10C | 10C | 7C,7G | 6C,7G | 3C,7G |
| | 0.06 | 10C | 10C | — | 8C,8G | 7G | 10C | 9C,9G | 7C,8G | 9C,9G | 10C | 7C,7G |
| | 0.25 | 10C | 10C | — | 9C,9G | 8G | 2C,3G | 10C | 10C | 10C | 10C | 10C |
| | 0.06 | 2C,3G | 10C | | 8C,8G | 7G | 10C | 9C,9G | 3C,7G | 7C,8G | 9C,8G | 4C,6G |
| | 0.25 | 3C,5G | 10C | | 9C,9G | 8G | 10C | 10C | 7C,8G | 9C,9G | 9C,9G | 8C,7G |
| CH₂SCH₃ —⌬— SO₂NHCONH— pyrimidine(CH₃)(OCH₃) | 0.25 | 2G | 7C,6G | — | 8C,7G | 5C,7G | 3C,4G | 0 | 2C,4G | 3C,5G | 10C | 1C,2G |
| | 0.25 | 2G | 1C,2G | | 2C,2G | 3G | 1C,2G | 0 | 1G | 0 | 3C,5G | 1C,2G |

Pre-emergence / Post-emergence sections as labeled in the original table.

TABLE D-continued

| Structure | Rate | | | | | | | | | | |
|---|---|---|---|---|---|---|---|---|---|---|---|
| ![structure with CH2S(O)CH3, SO2NHCONH, pyrimidine with 2 CH3] | 0.06 | 0 | 2C,2G | — | 7C,6G | 2G | 3C,2G | 1C,2G | 0 | 1C,2G | 3C,4G | 0 |

Pre-emergence

| | 0.06 | 2G | 5C,7G | — | 3C,7G | 3G | 3C,8G | 3G | 0 | 1C,2G | 3C,4G | 0 |

Post-emergence

| Structure | | | | | | | | | | | | |
|---|---|---|---|---|---|---|---|---|---|---|---|---|
| | 0.015 | 3C,4G | 10C | — | 10C | 2C,2G | 5C,4G | 2C,2G | 0 | 7C,8G | 10C | 2C,2G |
| | 0.06 | 10C | 10C | — | 10C | 7C,6G | 10C | 7C,6G | 2C,4G | | 10C | 8C,7G |

![structure with CH2SO2CH3, SO2NHCONH, pyrimidine with 2 OCH3]

Pre-emergence

| | 0.015 | 0 | 3C,5G | — | 4C,8G | 2G | 7C,9G | 2C,3G | 2C,2G | 8C,9G | 7C,7G | 3G |
| | 0.06 | 10C | 10C | — | 9C,9G | 3C,7G | 9C,9G | 7C,8G | 4C,7G | 9C,9G | 9C,9G | 7C,7G |

Post-emergence

| | 0.015 | 7C,6G | 10C | — | 10C | 0 | 8C,7G | 7C,6G | 0 | 10C | 10C | 7C,6G |
| | 0.06 | 8C,7G | 10C | — | 10C | 4C,5G | 10C | 10C | 3C,5G | 10C | 10C | 9C,8G |

![structure with CH2S(O)CH3, SO2NHCONH, pyrimidine with 2 OCH3]

Pre-emergence

| | 0.015 | 5C,4G | 9C,9G | — | 8C,8G | 3G | 9C,9G | 3C,5G | 2C,5G | 4C,8G | 7C,7G | 3C,4G |
| | 0.06 | 6C,7G | 10C | — | 10C | 3C,7G | 9C,9G | 7C,8G | 3C,8G | 9C,8G | 9C,9G | 4C,5G |

What is claimed is:
1. A compound selected from

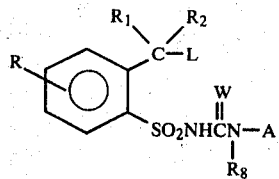

wherein

L is S(O)$_n$R$_7$ or OR$_9$;
R is H, F, Cl, Br, NO$_2$, CF$_3$, C$_1$–C$_3$ alkyl or C$_1$–C$_3$ alkoxy;
R$_1$ is H or C$_1$–C$_4$ alkyl;
R$_2$ is H or CH$_3$;
R$_7$ is C$_1$–C$_4$ alkyl;
R$_8$ is H, CH$_3$ or OCH$_3$;
R$_9$ is C$_1$–C$_6$ alkyl, C$_3$–C$_4$ alkenyl, CH$_2$CF$_3$, CF$_2$CF$_2$H or C$_5$–C$_6$ cycloalkyl;
n is 0, 1 or 2;
A is

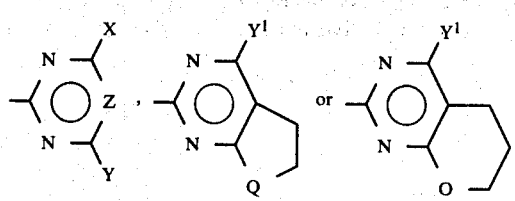

W is O or S;
X is H, Cl, Br, CH$_3$, CH$_2$CH$_3$, C$_1$–C$_3$ alkoxy, CF$_3$, SCH$_3$ or CH$_2$OCH$_3$;
Y is CH$_3$ or OCH$_3$;
Z is N, CH, CCl, CBr, CCN, CCH$_3$, CCH$_2$CH$_3$, CCH$_2$CH$_2$Cl or CCH$_2$CH=CH$_2$;
Y$^1$ is H, CH$_3$, OCH$_3$ or OCH$_2$CH$_3$; and
Q is O or CH$_2$;
and their agriculturally suitable salts; provided that when n is 1, then W is O; and when W is S, then R$_8$ is H.

2. A compound of claim 1 wherein Z is N, CH, CCl, CBr or CCH$_3$, W is O and R$_8$ is H or CH$_3$.

3. A compound of claim 2 wherein Z is N or CH, X is CH$_3$ or OCH$_3$, provided that when n is 1 or 2, then Z is CH.

4. A compound of claim 3 wherein A is

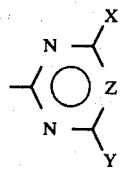

and R, R$_1$, R$_2$ and R$_8$ are H.

5. A compound of claim 4 wherein R$_9$ is C$_1$–C$_4$ alkyl.
6. A compound of claim 5 wherein R$_7$ and R$_9$ are CH$_3$.
7. The compound of claim, N-[(4,6-Dimethylpyrimidin-2-yl)aminocarbonyl]-2-methoxymethyl)benzenesulfonamide.
8. The compound of claim 1, N-[(4-Methoxy-6-methylpyrimidin-2-yl)aminocarbonyl]-2-(methoxymethyl)benzenesulfonamide.
9. The compound of claim 1, N-[(4,6-Dimethoxypyrimidin-2-yl)aminocarbonyl]-2-(methoxymethyl)benzenesulfonamide.
10. The compound of claim 1, N-[(4,6-Dimethyl-1,3,5-triazin-2-yl)aminocarbonyl]-2-(methoxymethyl)benzenesulfonamide.
11. The compound of claim 1, N-[(4-Methoxy-6-methyl-1,3,5-triazin-2-yl)aminocarbonyl]-2-(methoxymethyl)benzenesulfonamide.
12. The compound of claim 1, N-[(4,6-Dimethoxy-1,3,5-triazin-2-yl)aminocarbonyl]-2-(methoxymethyl)benzenesulfonamide.
13. The compound of claim 1, N-[(4,6-dimethylpyrimidin-2-yl)aminocarbonyl]-2-(methylthiomethyl)benzenesulfonamide.
14. The compound of claim 1, N-[(4-Methoxy-6-methylpyrimidin-2-yl)aminocarbonyl]-2-(methylthiomethyl)benzenesulfonamide.
15. The compound of claim 1, N-[(4,6-Dimethoxypyrimidin-2-yl)aminocarbonyl]-2-(methylthiomethyl)benzenesulfonamide.
16. The compound of claim 1, N-[(4,6-Dimethyl-1,3,5-triazin-2-yl)aminocarbonyl]-2-(methylthiomethyl)benzenesulfonamide.
17. The compound of claim 1, N-[(4-Methoxy-6-methyl-1,3,5-triazin-2-yl)aminocarbonyl]-2-(methylthiomethyl)benzenesulfonamide.
18. The compound of claim 1, N-[(4,6-Dimethoxy-1,3,5-triazin-2-yl)aminocarbonyl]-2-(methylthiomethyl)benzenesulfonamide.
19. The compound of claim 1, N-[(4,6-Dimethylpyrimidin-2-yl)aminocarbonyl]-2-(methylsulfinylmethyl)benzenesulfonamide.
20. The compound of claim 1, N-[(4-Methoxy-6-methylpyrimidin-2-yl)aminocarbonyl]-2-(methylsulfonylmethyl)benzenesulfonamide.
21. The compound of claim 1, N-[(4-Methoxy-6-methylpyrimidin-2-yl)aminocarbonyl]-2-(methylsulfinylmethyl)benzenesulfonamide.
22. The compound of claim 1, N-[(4,6-Dimethoxypyrimidin-2-yl)aminocarbonyl]-2-(methylsulfonylmethyl)benzenesulfonamide.
23. The compound of claim 1, N-[(4,6-Dimethoxypyrimidin-2-yl)aminocarbonyl]-2-(methylsulfinylmethyl)benzenesulfonamide.
24. The compound of claim 1, N-[(4,6-Dimethylpyrimidin-2-yl)aminocarbonyl]-2-(methylsulfonylmethyl)benzenesulfonamide.
25. The compound of claim 1, N-[(4,6-dimethoxypyrimidin-2-yl)aminocarbonyl]-2-(butoxymethyl)benzenesulfonamide.
26. The compound of claim 1, N-[(4,6-dimethoxypyrimidin-2-yl)aminocarbonyl]-2-(ethoxymethyl)benzenesulfonamide.
27. The compound of claim 1, N-[(4,6-dimethoxypyrimidin-2-yl)aminocarbonyl]-2-(1-methylpropyloxymethyl)benzenesulfonamide.
28. A composition suitable for controlling the growth of undesired vegetation which comprises an effective amount of a compound of claim 1 and at least one of the following: surfactant, solid or liquid diluent.
29. A composition suitable for controlling the growth of undesired vegetation which comprises an effective amount of a compound of claim 2 and at least one of the following: surfactant, solid or liquid diluent.
30. A composition suitable for controlling the growth of undesired vegetation which comprises an effective amount of a compound of claim 3 and at least one of the following: surfactant, solid or liquid diluent.

31. A composition suitable for controlling the growth of undesired vegetation which comprises an effective amount of a compound of claim 4 and at least one of the following: surfactant, solid or liquid diluent.

32. A composition suitable for controlling the growth of undesired vegetation which comprises an effective amount of a compound of claim 5 and at least one of the following: surfactant, solid or liquid diluent.

33. A composition suitable for controlling the growth of undesired vegetation which comprises an effective amount of a compound of claim 6 and at least one of the following: surfactant, solid or liquid diluent.

34. A composition suitable for controlling the growth of undesired vegetation which comprises an effective amount of the compound of claim 7 and at least one of the following: surfactant, solid or liquid diluent.

35. A composition suitable for controlling the growth of undesired vegetation which comprises an effective amount of the compound of claim 8 and at least one of the following: surfactant, solid or liquid diluent.

36. A method for controlling the growth of undesired vegetation which comprises applying to the locus to be protected an effective amount of a compound of claim 1.

37. A method for controlling the growth of undesired vegetation which comprises applying to the locus to be protected an effective amount of a compound of claim 2.

38. A method for controlling the growth of undesired vegetation which comprises applying to the locus to be protected an effective amount of a compound of claim 3.

39. A method for controlling the growth of undesired vegetation which comprises applying to the locus to be protected an effective amount of a compound of claim 4.

40. A method for controlling the growth of undesired vegetation which comprises applying to the locus to be protected an effective amount of a compound of claim 5.

41. A method for controlling the growth of undesired vegetation which comprises applying to the locus to be protected an effective amount of a compound of claim 6.

42. A method for controlling the growth of undesired vegetation which comprises applying to the locus to be protected an effective amount of the compound of claim 7.

43. A method for controlling the growth of undesired vegetation which comprises applying to the locus to be protected an effective amount of the compound of claim 8.

* * * * *